US009346854B2

(12) United States Patent
Shai et al.

(10) Patent No.: US 9,346,854 B2
(45) Date of Patent: May 24, 2016

(54) ANTI-INFLAMMATORY PEPTIDES AND USE THEREOF

(71) Applicant: Yeda Research and Development Co. Ltd., Rehovot (IL)

(72) Inventors: Yechiel Shai, Yehud (IL); Avner Fink, Rehovot (IL); Shay Yaari, Rehovot (IL); Tova Waks, Rehovot (IL); Zelig Eshhar, Rehovot (IL); Christopher J. Arnush, Rehovot (IL)

(73) Assignee: Yeda Research and Developement Co. Ltd., Rehovot (IL)

( * ) Notice: Subject to any disclaimer, the term of this patent is extended or adjusted under 35 U.S.C. 154(b) by 0 days.

(21) Appl. No.: 14/323,408

(22) Filed: Jul. 3, 2014

(65) Prior Publication Data

US 2014/0336105 A1  Nov. 13, 2014

Related U.S. Application Data

(63) Continuation of application No. PCT/IL2013/050022, filed on Jan. 8, 2013.

(60) Provisional application No. 61/584,339, filed on Jan. 9, 2012.

(51) Int. Cl.
*C07K 7/00* (2006.01)
*C07K 7/08* (2006.01)
*A61K 38/08* (2006.01)
*C07K 14/00* (2006.01)

(52) U.S. Cl.
CPC ... *C07K 7/08* (2013.01); *C07K 7/00* (2013.01); *C07K 14/001* (2013.01); *A61K 38/08* (2013.01)

(58) Field of Classification Search
CPC ........ A61K 38/08; C07K 14/001; C07K 7/00; C07K 7/08
USPC ............... 514/18.7, 1.4, 1.7, 21.3, 21.4, 21.5; 530/324, 325, 326, 327
See application file for complete search history.

(56) References Cited

U.S. PATENT DOCUMENTS

| 5,856,178 A | 1/1999 | White et al. |
| 2005/0187151 A1 | 8/2005 | Strom et al. |

FOREIGN PATENT DOCUMENTS

| WO | 2005060541 A2 | 7/2005 |
| WO | WO 2005/060541 | 7/2005 |
| WO | WO 2013/105089 | 7/2013 |

OTHER PUBLICATIONS de Planque et al, "Sensitivity of Single Membrane-Spanning alpha-Helical Peptides to Hydrophobic Mismatch with a Lipid Bilayer: Effects on Backbone Structure, Orientation, and Extent of Membrane Incorporation," Biochemistry, 2001, 40: 5000-5010.*
Martinez-Rodriguez et al, "Natural Occurrence and Industrial Applications of D-Amino Acids: An Overview," Chemistry and Biodiversity, 2010, 7: 1531-1548.*
Communication Under Rule 164(2)(a) EPC Dated May 28, 2015 From the European Patent Office Re. Application No. 13704635.5.
International Preliminary Report on Patentability Dated Jul. 15, 2014 From the International Bureau of WIPO Re. Application No. PCT/IL2013/050022.
International Search Report and the Written Opinion Dated Aug. 14, 2013 From the International Searching Authority Re. Application No. PCT/IL2013/050022.
Larrick et al. "A Novel Granulocyte-Derived Peptide With Lipopolysaccharide-Neutralizing Activity", Journal of Immunology, XP002236820, 152: 231-240, Jan. 1, 1994.
Rosenfeld et al. "Lipopolysaccharide (Endotoxin)-Host Defense Antibacterial Peptides Interactions: Role in Bacterial Resistance and Prevention of Sepsis", Biochimica et Biophysica Acta, XP027916016, 1758(9): 1513-1522, Sep. 1, 2006. Table 1.
Sharpe et al. "Organization of Model Helical Peptides in Lipid Bilayers: Insight Into the Behavior of Single-Span Protein Transmembrane Domains", Biophysical Journal, XP055061778, 83(1): 345-358, Jul. 2002. p. 346, r-h Col.
Strandberg et al. "Phase Diagrams of Systems With Cationic Alpha-Helical Membrane-Spanning Model Peptides and Dioleoylphosphatidylcholine", Advances in Colloid and Interface Science, XP055061820, 89-90: 239-261, Jan. 1, 2001. Table 1.
Benkirane et al., (1993) Antigenicity and immunogenicity of modified synthetic peptides containing D-amino acid residues. Antibodies to a D-enantiomer do recognize the parent L-hexapeptide and reciprocally. J Biol Chem 268(35): 26279-85.
Bhunia et al., (2008) Interactions of a designed peptide with lipopolysaccharide: Bound conformation and anti-endotoxic activity. Biochem Biophys Res Commun 369(3): 853-7.
Brandenburg et al., (2010) Molecular basis for endotoxin neutralization by amphipathic peptides derived from the alpha-helical cationic core-region of NK-lysin. Biophys Chem 150(1-3): 80-7.
Chen et al., (2005) Tachyplesin activates the classic complement pathway to kill tumor cells. Cancer Res 65(11): 4614-22.
David (2001) Towards a rational development of anti-endotoxin agents: novel approaches to sequestration of bacterial endotoxins with small molecules. J Mol Recognit 14(6): 370-87.
Eshhar et al., (1980) Generation of hybridomas secreting murine reaginic antibodies of anti-DNP specificity. J Immunol 124(2): 775-80.
Funderburg et al., (2007) Human -defensin-3 activates professional antigen-presenting cells via Toll-like receptors 1 and 2. Proc Natl Acad Sci U S A 104(47): 18631-5.

(Continued)

*Primary Examiner* — Julie Ha

(57) ABSTRACT

Isolated peptides of 13-30 amino acids comprising 5-9 consecutive repeats of the amino acid pair Alanine-Leucine or Alanine-Valine are provided. The peptides further comprise a stretch of 1-3 Lysine residues present at least at one of the peptide's termini, wherein the only Lysine residue in the isolated peptide is present at the stretch of 1-3 Lysine residues. Pharmaceutical compositions comprising same, methods of treating inflammatory conditions and allergic reactions, as well as methods of neutralizing the activity of lypopolysaccharides are also provided.

14 Claims, 9 Drawing Sheets

(56) References Cited

OTHER PUBLICATIONS

Larrick et al., (1994) A novel granulocyte-derived peptide with lipopolysaccharide-neutralizing activity. J Immunol 152 (1): 231-40.

Makovitzki et al., (2009) Suppression of human solid tumor growth in mice by intratumor and systemic inoculation of histidine-rich and pH-dependent host defense-like lytic peptides. Cancer Res 69(8): 3458-63.

Merrifield (1963) Solid phase peptide synthesis. I. The synthesis of a tetrapeptide. J Am Chem Soc 85 (14): 2149-2154.

Miller et al., (2005) Lipopolysaccharide sequestrants: structural correlates of activity and toxicity in novel acylhomospermines. J Med Chem 48(7): 2589-99.

Nunomura et al., (2005) Role of the FcepsilonRI beta-chain ITAM as a signal regulator for mast cell activation with monomeric IgE. Int Immunol 17(6): 685-94.

Papo et al., (2002) The consequence of sequence alteration of an amphipathic alpha-helical antimicrobial peptide and its diastereomers. J Biol Chem 277(37): 33913-21.

Rosenfeld and Shai (2006) Lipopolysaccharide (Endotoxin)-host defense antibacterial peptides interactions: role in bacterial resistance and prevention of sepsis. Biochim Biophys Acta 1758(9): 1513-22.

Rosenfeld et al., (2006) Endotoxin (lipopolysaccharide) neutralization by innate immunity host-defense peptides. Peptide properties and plausible modes of action. J Biol Chem 281(3): 1636-43.

Rosenfeld et al., (2008) Parameters involved in antimicrobial and endotoxin detoxification activities of antimicrobial peptides. Biochemistry 47(24): 6468-78.

Rosenfeld et al., (2010) Effect of the hydrophobicity to net positive charge ratio on antibacterial and anti-endotoxin activities of structurally similar antimicrobial peptides. Biochemistry 49(5): 853-61.

Sharpe et al., (2002) Organization of model helical peptides in lipid bilayers: insight into the behavior of single-span protein transmembrane domains. Biophys J 83(1): 345-58.

Strandberg et al., (2001) Phase diagrams of systems with cationic alpha-helical membrane-spanning model peptides and dioleoylphosphatidylcholine. Adv Colloid Interface Sci 89-90: 239-61.

Wexler-Cohen et al., (2005) The role of the N-terminal heptad repeat of HIV-1 in the actual lipid mixing step as revealed by its substitution with distant coiled coils. Biochemistry 44(15): 5853-61.

Zelezetsky et al., (2005) Controlled alteration of the shape and conformational stability of alpha-helical cell-lytic peptides: effect on mode of action and cell specificity. Biochem J 390(Pt 1): 177-88.

Zheng et al., (2010) Identification of a new anti-LPS agent, geniposide, from Gardenia jasminoides Ellis, and its ability of direct binding and neutralization of lipopolysaccharide in vitro and in vivo. Int Immunopharmacol 10(10): 1209-19.

Communication Pursuant to Article 94(3) EPC Dated Oct. 23,2015 From the European Patent Office Re. Application No. 13704635.5.

\* cited by examiner

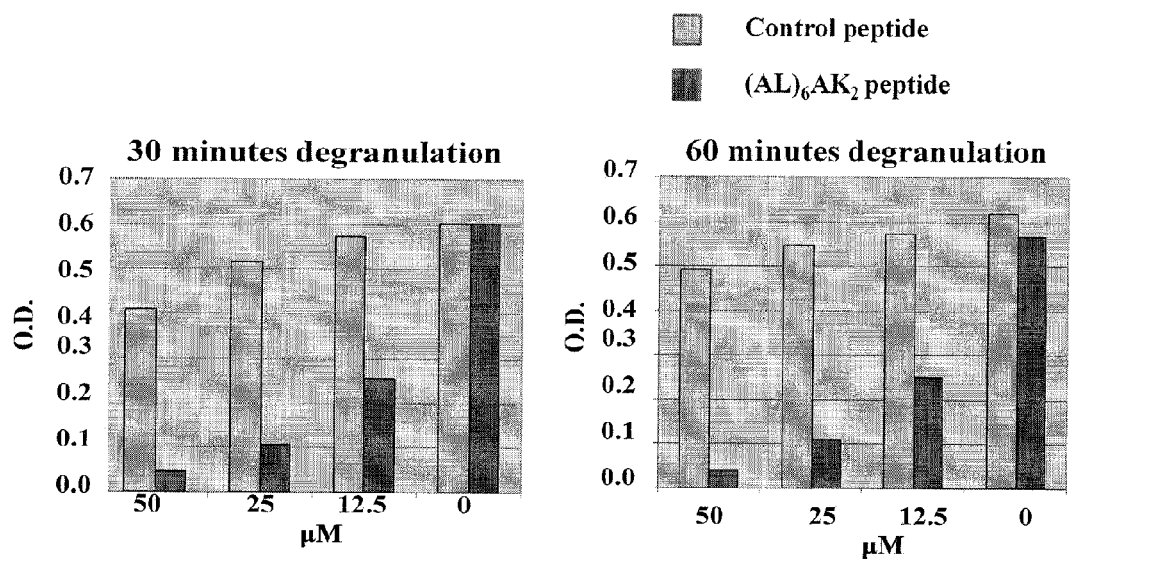
Figure 6A
Figure 6B
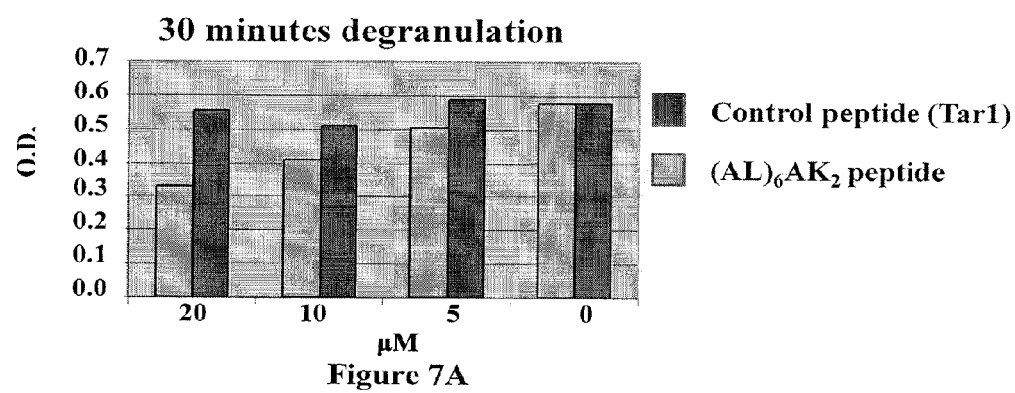
Figure 7A
Figure 7B

SEQUENCE LISTING

```
<160> NUMBER OF SEQ ID NOS: 17

<210> SEQ ID NO 1
<211> LENGTH: 20
<212> TYPE: PRT
<213> ORGANISM: Artificial
<220> FEATURE:
<223> OTHER INFORMATION: Synthetic peptide

<400> SEQUENCE: 1

Lys Lys Ala Leu Ala Leu Ala Leu Ala Leu Ala Leu Ala Leu Ala Leu
1               5                   10                  15

Ala Leu Lys Lys
            20

<210> SEQ ID NO 2
<211> LENGTH: 20
<212> TYPE: PRT
<213> ORGANISM: Artificial
<220> FEATURE:
<223> OTHER INFORMATION: Synthetic peptide

<400> SEQUENCE: 2

Ala Leu Ala Leu Ala Leu Ala Leu Ala Leu Ala Leu Ala Leu Ala Leu
1               5                   10                  15

Ala Leu Lys Lys
            20

<210> SEQ ID NO 3
```

```
<211> LENGTH: 20
<212> TYPE: PRT
<213> ORGANISM: Artificial
<220> FEATURE:
<223> OTHER INFORMATION: Synthetic peptide

<400> SEQUENCE: 3

Lys Ala Leu Ala Leu Ala Leu Ala Leu Ala Leu Ala Leu Ala Leu Ala
1               5                   10                  15

Leu Ala Leu Lys
            20

<210> SEQ ID NO 4
<211> LENGTH: 15
<212> TYPE: PRT
<213> ORGANISM: Artificial
<220> FEATURE:
<223> OTHER INFORMATION: Synthetic peptide

<400> SEQUENCE: 4

Ala Leu Ala Leu Ala Leu Ala Leu Ala Leu Ala Leu Ala Leu Lys
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic peptide

<400> SEQUENCE: 5

Lys Lys Ala Leu Ala Leu Ala Leu Ala Leu Ala Leu Ala Lys Lys
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic peptide

<400> SEQUENCE: 6

Ala Leu Ala Leu Ala Leu Ala Leu Ala Leu Ala Leu Ala Lys Lys
1               5                   10                  15

<210> SEQ ID NO 7
<211> LENGTH: 16
<212> TYPE: PRT
<213> ORGANISM: Artificial
<220> FEATURE:
<223> OTHER INFORMATION: Synthetic peptide

<400> SEQUENCE: 7

Lys Ala Leu Ala Leu Ala Leu Ala Leu Ala Leu Ala Leu Ala Leu Lys
1               5                   10                  15

<210> SEQ ID NO 8
<211> LENGTH: 20
<212> TYPE: PRT
<213> ORGANISM: Artificial
<220> FEATURE:
<223> OTHER INFORMATION: Synthetic peptide

<400> SEQUENCE: 8

Lys Lys Ala Val Ala Val Ala Val Ala Val Ala Val Ala Val Ala Val
1               5                   10                  15
```

Ala Val Lys Lys
            20

<210> SEQ ID NO 9
<211> LENGTH: 20
<212> TYPE: PRT
<213> ORGANISM: Artificial
<220> FEATURE:
<223> OTHER INFORMATION: Synthetic peptide

<400> SEQUENCE: 9

Lys Ala Leu Ala Leu Ala Leu Lys Ala Leu Ala Leu Lys Ala Leu Ala
1               5                   10                  15

Leu Ala Leu Lys
            20

<210> SEQ ID NO 10
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (10)..(10)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MISC_FEATURE
<222> LOCATION: (18)..(18)
<223> OTHER INFORMATION: D-Leu

<400> SEQUENCE: 10

Lys Lys Ala Leu Ala Leu Ala Leu Ala Leu Ala Leu Ala Leu Ala Leu
1               5                   10                  15

Ala Leu Lys Lys
            20

<210> SEQ ID NO 11
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (10)..(10)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MISC_FEATURE
<222> LOCATION: (18)..(18)
<223> OTHER INFORMATION: D-Leu

<400> SEQUENCE: 11

Ala Leu Ala Leu Ala Leu Ala Leu Ala Leu Ala Leu Ala Leu Ala Leu
1               5                   10                  15

Ala Leu Lys Lys
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic peptide

<400> SEQUENCE: 12

Lys Lys Ala Ala Ala Ala Ala Ala Ala Ala Ala Ala Ala Ala Ala Ala
1               5                   10                  15

Ala Ala Lys Lys
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide

<400> SEQUENCE: 13

Leu Ala Leu Ala Leu Ala Leu Ala Leu Ala Leu Ala Leu Ala Leu Ala
1               5                   10                  15

Leu Ala Leu Lys
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (10)..(10)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MISC_FEATURE
<222> LOCATION: (18)..(18)
<223> OTHER INFORMATION: D-Leu

<400> SEQUENCE: 14

Lys Lys Ala Leu Ala Leu Ala Leu Ala Leu Ala Leu Ala Leu Ala Leu
1               5                   10                  15

Ala Leu Lys Lys
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: D-Leu

```
<220> FEATURE:
<221> NAME/KEY: MISC_FEATURE
<222> LOCATION: (10)..(10)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MISC_FEATURE
<222> LOCATION: (18)..(18)
<223> OTHER INFORMATION: D-Leu

<400> SEQUENCE: 15

Ala Leu Ala Leu Ala Leu Ala Leu Ala Leu Ala Leu Ala Leu Ala Leu
1               5                   10                  15

Ala Leu Lys Lys
            20

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Lys Lys Ala Leu Ala Leu Ala Leu Lys Lys
1               5                   10

<210> SEQ ID NO 17
<211> LENGTH: 25
<212> TYPE: PRT
<213> ORGANISM: Artificial Sequence
<220> FEATURE:
<223> OTHER INFORMATION: Synthetic peptide

<400> SEQUENCE: 17

Lys Lys Ala Leu Ala Leu Ala Leu Ala Leu Ala Leu Ala Leu Ala Leu
1               5                   10                  15

Ala Leu Ala Leu Ala Leu Ala Lys Lys
            20                  25
```

US 9,346,854 B2

ANTI-INFLAMMATORY PEPTIDES AND USE THEREOF

FIELD OF THE INVENTION

The present invention relates to peptides comprising lysine, alanine, leucine and valine, pharmaceutical compositions comprising same, and uses thereof for treating inflammatory conditions and allergy.

BACKGROUND OF THE INVENTION

Antimicrobial Peptides

Lipopolysaccharides (LPS) and lipoteichoic acid (LTA) are recognized as pathogen-associated molecular patterns (PAMPs) by pattern recognition receptors such as Toll-Like Receptors (TLRs). These receptors are expressed on innate immune cells, mainly by mononuclear phagocytes (monocytes and macrophages). Their activation by PAMPs results in secretion of pro-inflammatory cytokines such as tumor necrosis factor-alpha (TNF-α), interleukin 6 (IL-6) and IL-1β. Although this is a normal and beneficial response towards an invading pathogen, an unbalanced or an over-stimulation of this system can lead to sepsis, organ failure and death.

Antimicrobial peptides (AMPs), also named host defense peptides (HDPs), are central effector molecules of the innate immune system and are produced by the host as an initial response to combat pathogen infections. In addition to their classical lytic mode of action, some peptides have been shown to possess additional functions including anti cancer activity, complement activation, direct activation of TLRs and neutralizing LPS toxicity. Despite this large repertoire of diverse AMPs, there is still only limited knowledge about the crucial parameters involved in LPS neutralization, and the relation to antimicrobial activity.

Classically, AMPs were characterized for their ability to target and lyse bacterial membranes of both Gram negative and Gram positive bacteria. In recent years, there is growing evidence that some AMPs are able to neutralize the cytotoxicity of LPS. For example, lactoferrin, LL37 (corresponding to amino acids 134-170 of the human cationic antimicrobial protein 18 (hCAP18)) and temporins neutralize LPS while other AMPs such as magainin do not have this ability. Mode of action studies for these peptides revealed different mechanisms of LPS neutralization depending on the type of AMPs used. Most studies examined the interactions of the peptides with lipid A, the hydrophobic anchor of LPS to the membrane. These studies emphasized the interaction of the positive charges on the peptides with the phosphate head groups on the lipid A as well as the hydrophobic interaction of the peptide backbone with the acyl chains of the lipid A.

Previous studies have focused on hydrophobicity, charge and oligomerization as important parameters for LPS neutralization (David et al. J Mol Recognit 14, 370-87, 2001; Rosenfeld et al. Biochemistry 49, 853-61, 2010; Miller et al. J Med Chem 48, 2589-99, 2005; Brandenburg et al. Biophys Chem 150, 80-7, 2010). Bioinformatic analysis of sequences that are conserved in LPS binding proteins suggested a tri-peptide motif of hydrophobic/aromatic-basic-hydrophobic that is important for LPS recognition (Bhunia et al. Biochem Biophys Res Commun 369, 853-7, 2008). Papo et at (Papo et al. J Biol Chem 277, 33913-21, 2002) reported a segregated peptide composed of only leucines and lysines and suggests that hydrophobicity is also a very important parameter for toxicity and membrane activity. Studying de novo designed peptides as well as native antimicrobial peptides demonstrated that endotoxin neutralization properties are more complex than simply binding to LPS. For example, LL37 retained its neutralization activity even when not in direct contact with LPS (Rosenfeld et al. J Biol Chem 281, 1636-43, 2006). To date, the exact properties correlating LPS neutralization and antimicrobial activity of peptides are still not fully understood.

Allergic Conditions

A large and increasing proportion of the population in industrialized countries suffer from allergies. The current estimate for this debilitating condition is one in three people and a large proportion of this population is notably children. The pathogenesis of allergy is mediated by dysregulated triggering of IgE-mediated immune responses following repeated encounters with environmental antigens. IgE-mediated allergies are triggered by binding of IgE to the high affinity IgE receptor (FcεRI), which is expressed on effector mast cells, basophils and activated eosinophils. As a result of these high affinity interactions, stable FcεRI:IgE complexes are displayed on the surface of effector cells. Exposure to allergens leads to cross-linking and eventually clustering of IgE:FcεRI complexes, thus triggering effector cell activation, degranulation and release of stored pro-allergenic mediators that leads to the initiation of an allergic response.

Common environmental allergens which induce anaphylactic hypersensitivity are found in pollen, foods, house dust mites, animal danders, fungal spores and insect venoms. Atopic allergy is associated with anaphylactic hypersensitivity and includes the disorders, e.g., asthma, allergic rhinitis and conjunctivitis (hay fever), eczema, urticaria and food allergies. Further, an allergic reaction may lead to a dangerous life-threatening condition such as anaphylactic shock, which may be provoked by insect stings or parenteral medication.

None of the background art discloses or suggests that peptides consisting essentially of lysine, alanine, leucine and/or valine are useful as anti-inflammatory agents, particularly for treating microbial infections and allergic responses.

There exists a long-felt need for more effective means of curing or ameliorating inflammatory pathologies. Sepsis, e.g., is the most frequent cause of mortality in hospitalized patients. The development of new anti-inflammatory peptides capable of selectively treating said pathologies with minimal side effects is therefore desirable.

SUMMARY OF THE INVENTION

The present invention relates to peptides comprising or consisting essential of leucine, valine, and lysine and alanine, pharmaceutical compositions comprising same and use thereof for treating, ameliorating or preventing an inflammatory condition in a subject. The peptides are particularly useful in treating IgE-mediated allergies. In addition, said peptides are useful for treating inflammatory conditions including but not limited to sepsis.

The present invention is based, in part, on the unexpected discovery that peptides consisting of lysine, alanine, leucine or valine demonstrate anti-inflammatory activity at nanomolar concentrations with minimal toxicity. It is now disclosed, for the first time, that the peptides of the present invention inhibit TNFα secretion in macrophages stimulated with lipopolysaccharide (LPS also known as endotoxin) or lipoteichoic acid (LTA). Further, the peptides show a strong binding affinity to LPS, and are remarkably non-toxic in both in vivo and in vitro models. A single dose of an exemplary peptide was unexpectedly able to inhibit septic shock in mice induced by purified LPS or by whole heat-killed *E. coli*.

It is further disclosed that the peptides of the present invention inhibit FcεRI-mediated degranulation and thereby the onset of immediate allergic responses. Further, the peptides of the invention inhibited allergic reactions in vivo in two well established systems. The peptides inhibited almost completely passive cutaneous anaphylaxis (PCA) within 15-30 minutes. Further, a single injection of said peptides inhibited anaphylactic shock induction by an allergen (ovalbumin (OVA))-induced anaphylaxis model.

Thus, the present invention provides peptides comprising or consisting essentially of leucine, valine, lysine and alanine, and pharmaceutical compositions comprising same useful for treating an inflammatory condition in a subject. In some embodiments, the peptides comprise or consists of 5-9 consecutive repeats of an amino acid pair selected from the group consisting of: Alanine-Leucine, Leucine-Alanine, Alanine-Valine and Valine-Alanine, and a stretch of 1-3 Lysine residues present at-least at one of the peptide's termini, wherein the only Lysine residue in the isolated peptide is present at the stretch of 1-3 Lysine residues.

In some embodiments, the peptides of the invention consist of leucine, lysine and alanine. In other embodiments, the peptides of the invention consist of valine, lysine and alanine According to some embodiments, the peptide consists of 15-35 amino acids. According to another embodiment, the peptide consists of 15-30 amino acids. According to particular embodiments, the peptide consists of 15-25 amino acids. According to another particular embodiment, the peptide consists of 18-22 amino acids. According to an exemplary embodiment, the peptide consists of 20 amino acids. According to yet another exemplary embodiment, the peptide consists of 15 amino acids.

According to one aspect, the present invention provides an isolated peptide of 13-30 amino acids comprising at least one terminal Lysine residue and 5-9 repeats of an amino acid pair comprising Alanine and $X_1$, wherein $X_1$ is Leucine or Valine. In some embodiments, there is provided an analog, derivative or a salt of said peptide. In another embodiment, the amino acid repeats are consecutive (i.e., adjacent to one another).

In some embodiments, the peptide comprises at least one terminal Lysine residues at said peptide's N-terminus, C-terminus or both. In specific embodiments, the peptide comprises a sequence of 1-3 Lysine residues at at-least one terminus. In another embodiment, the peptide comprises 1-3 Lysine residues both at said peptide's N-terminus and C-terminus. In another embodiment, said at least one terminal Lysine residue of the peptide is 1-2 Lysine residues contiguous to the amino acid pair repeats.

According to one embodiment, the amino acid pair is Alanine-$X_1$, wherein $X_1$ is Leucine or Valine. In a particular embodiment, said amino acid pair is Alanine-Leucine. In another particular embodiment, said amino acid pair is Alanine-Valine.

According to another embodiment, the amino acid pair is $X_1$-Alanine, wherein $X_1$ is Leucine or Valine. In a particular embodiment, said amino acid pair is Leucine-Alanine. In another particular embodiment, said amino acid pair is Valine-Alanine.

According to another embodiment, the peptide comprises 5 repeats of said amino acid pair. According to another embodiment, the peptide comprises 6 repeats of said amino acid pair. According to another embodiment, the peptide comprises 7 repeats of said amino acid pair. According to another embodiment, the peptide comprises 8 repeats of said amino acid pair. According to another embodiment, the peptide comprises 9 repeats of said amino acid pair.

According to another embodiment, the peptide comprises the formula of $K_n(AX_1)_mX_2K_n$, wherein $X_1$ is Leucine (L) or Valine (V), $X_2$ is absent or Alanine, n, at each occurrence is independently 0-2 with the proviso that at least one terminal Lysine (K) is present, and m is 6-9. According to another embodiment, the peptide consists of $K_n(AX_1)_mX_2K_n$, wherein $X_1$ is Leucine (L) or Valine (V), $X_2$ is absent or Alanine, n, at each occurrence is independently 0-2 with the proviso that at least one terminal Lysine (K) is present, and m is 5-9.

According to another embodiment, the peptide is selected from the group consisting of:

KK(AL)$_8$KK; (SEQ ID NO: 1)

(AL)$_9$KK; (SEQ ID NO: 2)

K(AL)$_9$K; (SEQ ID NO: 3)

(AL)$_7$K; (SEQ ID NO: 4)

KK(AL)$_5$AKK; (SEQ ID NO: 5)

(AL)$_6$AKK; (SEQ ID NO: 6)

K(AL)$_6$AK; (SEQ ID NO: 7)
and

KK(AV)$_8$KK. (SEQ ID NO: 8)

According to another embodiment, the peptide comprises the formula of $K_n(AL)_mK_n$, wherein n, at each occurrence is independently 0-2 with the proviso that at least one terminal Lysine (K) is present, and m is 6-9. According to another embodiment, the peptide consists of $K_n(AL)_mK_n$, wherein n, at each occurrence is independently 0-2 with the proviso that at least one terminal Lysine (K) is present, and m is 6-9.

According to another embodiment, the peptide is selected from the group consisting of:

KK(AL)$_8$KK; (SEQ ID NO: 1)

(AL)$_9$KK; (SEQ ID NO: 2)

K(AL)$_9$K; (SEQ ID NO: 3)
and (AL)$_7$K. (SEQ ID NO: 4)

According to an exemplary embodiment, the peptide comprises the amino acid sequence as set forth in KK(AL)$_8$KK (SEQ ID NO: 1). According to yet another exemplary embodiment, the peptide consists of the amino acid sequence as set forth in KK(AL)$_8$KK (SEQ ID NO: 1).

According to another embodiment, the peptide comprises or consists of the formula $K_n(AL)_mAK_n$, wherein n, at each occurrence is independently 0-2 with the proviso that at least one terminal Lysine (K) is present, and m is 5-9.

According to some embodiment, the peptide is selected from the group consisting of:

KK(AL)₅AKK; (SEQ ID NO: 5)

(AL)₆AKK; (SEQ ID NO: 6)
and

K(AL)₆AK. (SEQ ID NO: 7)

According to another embodiment, the peptide comprises or consists of the formula of $K_n(AV)_mK_n$, wherein n, at each occurrence is independently 0-2 with the proviso that at least one terminal Lysine (K) is present, and m is 6-9. According to another embodiment, the peptide comprises the amino acid sequence as set forth in KK(AV)₈KK (SEQ ID NO: 8). According to another embodiment, the peptide consists of the amino acid sequence as set forth in KK(AV)₈KK (SEQ ID NO: 8).

According to another embodiment, the peptide comprises at least one D amino acid. According to yet another embodiment, the peptide comprises 1-5 D amino acids.

According to another aspect, the present invention provides a pharmaceutical composition comprising as an active ingredient an isolated peptide of 13-30 amino acids comprising at least one Lysine residue and 5-9 repeats of an amino acid pair comprising Alanine and $X_1$, wherein $X_1$ is Leucine or Valine, and a pharmaceutically acceptable carrier. In some embodiments, there is provided a pharmaceutical composition comprising as an active ingredient an analog, derivative or a salt of said peptide.

According to another aspect, the present invention provides a peptide comprises an isolated peptide of 20-30 amino acids comprising the amino acid sequence as set forth in K(AL)₃K(AL)₂K(AL)₃K (SEQ ID NO: 9). In some embodiments, there is provided an analog, derivative or a salt of said peptide. In another embodiment, the present invention provides a pharmaceutical composition comprising as an active ingredient said isolated peptide, and a pharmaceutically acceptable carrier.

According to another aspect, the present invention provides a method of neutralizing the activity of lipopolysaccharides (LPS) endotoxin in a subject in need thereof comprising administering to the subject a therapeutically acceptable amount of the pharmaceutical composition of the present invention. In some embodiments, the method is useful for preventing, neutralizing or reducing endotoxemia or endotoxin-induced septic shock in said subject.

According to another aspect, the present invention provides a method of treating an inflammatory condition in a subject in need thereof comprising administering to the subject a therapeutically acceptable amount of the pharmaceutical composition of the present invention.

According to one embodiment, the inflammatory condition is caused by a microbial infection. According to some embodiments, the microbe is a Gram-negative bacterium. According to other embodiments, said microbe is a Gram-positive bacterium.

According to another embodiment, the inflammatory condition is selected from the group consisting of systemic inflammatory response syndrome (SIRS), sepsis, septicemia and septic shock.

According to another embodiment, the inflammatory condition is a mast cell-related disease. According to another embodiment, the inflammatory condition is an allergic reaction. According to another embodiment, the allergic reaction is an IgE-mediated allergic disorder.

According to another embodiment, the IgE-mediated allergic disorder is selected from the group consisting of: allergy-induced asthma, hypersensitivity, eczema conjunctivitis, urticaria, rhinorrhea, rhinitis gastroenteritis, pemphigus vulgaris, atopic dermatitis, eosinophilia, allergic bronchopulmonary aspergillosis, glomerular nephritis. Each possibility is a separate embodiment of the invention.

Additional disorders or disease having an IgE mediated component which may benefit from symptomatic relief by the compositions of the invention include, but are not limited to, parasitic diseases, interstitial cystitis, hyper-IgE syndrome and IgE myeloma.

According to another aspect there is provided the isolated peptide of the invention or a pharmaceutical composition comprising same for use in treating an inflammatory condition.

According to yet another aspect there is provided use of the isolated peptide of the invention or a pharmaceutical composition comprising same for the preparation of a medicament for treating an inflammatory condition.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2A shows different lengths of peptides (20, 15, 10 mer) compared with a set charge (+5). FIG. 2B shows different number of charges (+2, +3 and +5) compared with a set length (20 mer). FIG. 2C shows charge placement and D-amino acid substitutions compared with a set charge (+5) and length (20 mer). For all experiments peptide concentration used was 20 μM.

FIG. 3A shows different concentrations of LPS (from 1.56 to 100 μM) were added to 4-Fluoro-7-nitrobenzofurazan (NBD)-labeled peptides (1 μM) and the fluorescence was recorded. (□) $K_2(AL)_5AK_2$, (◇) 4D-$K_2(AL)_8K_2$, (△) K(AL)₃K(AL)₂K(AL)₃K, (○) $K_2(AL)_8K_2$, (⊖) K(AL)₉K. NBD excitation was set on 467 nm, emission was set on 530 nm. FIG. 3B shows representative peptides with low ($K_2(AL)_8K_2$) or high ($K_2(AL)_5AK_2$) bmax were examined for their aggregation state in LPS solution. Fluorescence of rhodmaine labeled peptides in LPS solution was monitored before and after the addition of ProteaseK (indicated by a black arrow). Maximal change in fluorescence was calculated after 60 minutes. FIG. 3C is a chart of maximal change % showing ($K_2(AL)_8K_2$) and ($K_2(AL)_5AK_2$).

FIG. 4A) $K_2(AL)_8K_2$, FIG. 4B) $K_2(AL)_5AK_2$, FIG. 4C) $K_2(AL)_3K_2$, FIG. 4D) $K_2(AV)_8K_2$ and FIG. 4E) $K(AL)_3K(AL)_2K(AL)_3K$ (FIG. 5C) Recovery time for sepsis induced by heat killed *E. coli*. Mice were scored on the severity of sepsis (n=11).

FIGS. 6A-6B depict the affect of $(AL)_6AK_2$ peptide on IgE mediated degranulation (as measured by the enzymatic activity of β-hexoseaminidase released from rat basophile leukemia (RBL) cells into the assay medium. (FIG. 6A) Incubation for 30 min or (FIG. 6B) 60 min in a degranulation buffer. 0=treated with detergent 1% TritonX to represent 100% β-hexoseaminidase release. Assay was performed in triplicates.

FIGS. 7A-7B depict the affect of $(AL)_6AK_2$ peptide on anti-FcεRI antibody mediated degranulation of RBL-2H3 cells. RBL-2H3 cells were incubated with different concentrations of $(AL)_6AK_2$ or a control peptide (Tar1 TM peptide) in the presence of diluted 52.1 anti-FcεRI mAb for 2 hrs.

DETAILED DESCRIPTION OF THE INVENTION

Figure 1A:
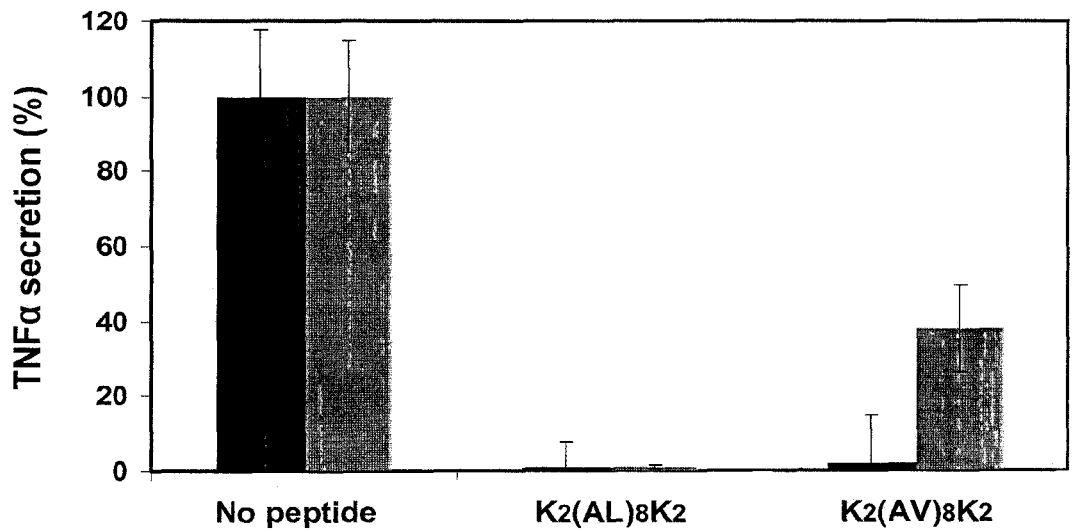
FIG. 1A depicts inhibition of TNFα secretion upon stimulation of RAW264.7 macrophages with LPS (light gray columns) and LTA (dark gray columns) using the $K_2(AL)_8K_2$ or $K_2(AV)_8K_2$ peptide. For both peptides tested a single concentration of 20 μM was used.

The present invention relates to peptides comprising or consisting essentially of lysine, alanine, valine and leucine. The present invention further relates to pharmaceutical compositions comprising same useful in treating, ameliorating or preventing an inflammatory condition in a subject, including but not limited IgE-induced allergies and septic shock.

As exemplified herein below, a series of peptides were designed where peptide length, hydrophobicity, charge, position of charge, and amino acid chirality could be easily varied. Surprisingly, a 20-mer hydrophobic peptide consisting of Alanine-Leucine (AL) repeats with flanking lysine residues showed potent LPS neutralization with low cytotoxicity (Example 1, FIG. 1A-B). A similar peptide comprising Alanine-Alanine (AA) repeats was not active, thus indicating a crucial role for hydrophobicity in LPS neutralization.

Previous studies have focused on hydrophobicity, charge and oligomerization as important parameters for LPS neutralization (David, 2001 ibid; Rosenfeld, 2010 ibid; Miller, 2005 ibid; Brandenburg, 2010 ibid). The peptides of the present invention are comparatively less hydrophobic peptide, and were not observed to be membrane active or toxic. Decreasing hydrophobicity even further by testing a peptide composed only of alanine and lysines resulted in a loss of LPS neutralization activity. An optimal hydrophobicity is thus necessary for high activity and low toxicity.

As shown herein below (Example 2), several parameters (e.g., peptide length and number of charges) are crucial for the peptide's LPS neutralization activity. It is further indicated that an ideal combination for a neutralizing peptide would be high affinity with α-helical structure and strong oligomerization ability. While dynamic interplay of these parameters, prediction algorithms for optimal peptide sequences are very complex, the present invention has revealed how key modifications can affect activity and toxicity and this information can serve as a guideline for future design strategies.

As exemplified herein below (Example 5), a model peptide under the formula $K_n(AL)_mK_n$ (wherein n at each occurrence is independently 0-2, and m is 6-9), was tested in vivo using two different murine models of sepsis. The mortality rates observed in the murine models represent fairly accurately the mortality rate of 30-50% observed in hospitals with patients receiving the best supportive care (Cohen, 2002). In the first model, purified LPS, in combination with D-galactosamine to temporarily suppress the liver function, caused animals to die within 24 hours. The second model involving an injection of only heat killed bacteria caused death up to four days post injection. Surprisingly, in both model systems the animals treated with the $KK(AL)_8KK$ (SEQ ID NO: 1) peptide completely recovered, indicating that said peptide can protect against both simple and complex challenges.

Further, very low toxicity was observed in vivo: Mice injected intravenously with up to 100 mg/kg of our peptide, a magnitude of 10 fold higher than the treatment dose, showed no adverse signs of toxicity. This is unique in comparison to the majority of antimicrobial peptides and de novo designed peptides that exhibit a small therapeutic window where the toxic dose is close to the effective dose (Papo et al., 2006; Zelezetsky et al. Biochem J 390, 177-88, 2005).

As further exemplified herein, the peptides of the invention inhibit FcεRI-mediated degranulation and thereby the onset of immediate allergic responses. Said peptides inhibited almost completely passive cutaneous anaphylaxis (PCA) within 15-30 minutes (Example 7). Further, a single injection of said peptides inhibited development of anaphylactic shock in an allergen (ovalbumin (OVA))-induced anaphylaxis model (Example 8).

Thus, the present invention provides peptides comprising or consisting essentially of leucine, valine, lysine and alanine, and pharmaceutical compositions comprising same useful for treating an inflammatory condition in a subject. In some embodiments, the peptides of the invention comprise, consist essentially of, or consist of leucine, lysine and alanine. In other embodiments, the peptides of the invention comprise, consist essentially of, or consist of valine, lysine and alanine.

According to some embodiments, the present invention provides an isolated peptide of 13-30 amino acids comprising 5-9 consecutive repeats of an amino acid pair selected from the group consisting of: Alanine-Leucine, Leucine-Alanine, Alanine-Valine and Valine-Alanine, and a stretch of 1-3 Lysine residues present at-least at one of the peptide's termini, wherein the only Lysine residue in the isolated peptide is present at the stretch of 1-3 Lysine residues.

According to additional embodiments, the peptides of the present invention comprise 13-30 amino acids consisting of at least one terminal Lysine residue and at least 11 amino acids selected from Alanine and $X_1$, wherein $X_1$ is Leucine and/or Valine. In some embodiments, $X_1$ is Leucine. In some embodiments, $X_1$ is Valine.

In additional embodiments, the peptides of the invention comprise Alanine, Leucine, Valine and Lysine residues. In another embodiment, the peptides of the invention consist of Alanine, Leucine, Valine and Lysine residues. In another embodiment, the peptide consists of amino acid residues Alanine, Leucine and Lysine. In another embodiment, the peptide consists of amino acid residues Alanine, Valine and Lysine.

According to another embodiment, the present invention provides an isolated peptide of 13-30 amino acids comprising at least one Lysine residue and 6-9 repeats of an amino acid pair comprising Alanine and $X_1$, wherein $X_1$ is Leucine or Valine. In another embodiment, there is provided an analog, derivative or a salt of said peptide.

According to another embodiment, the peptide comprises the formula of $K_n((AX_1)_mX_2)_zK_n$, wherein $X_1$ is Leucine (L) or Valine (V), $X_2$ is Lysine (K), Alanine (A) or absent, n, at each occurrence is independently 0-3 with the proviso that at least one terminal Lysine (K) is present, z is 1-3 and m is 2-9. In one embodiment, $X_2$ is Alanine, z is 1 and m is 5-6. In another embodiment, $X_2$ is Lysine, z is 3 and m is independently 2-3.

According to another embodiment, the peptide is selected from the group consisting of:

KK(AL)$_8$KK;  (SEQ ID NO: 1)

(AL)$_9$KK;  (SEQ ID NO: 2)

K(AL)$_9$K;  (SEQ ID NO: 3)

(AL)$_7$K;  (SEQ ID NO: 4)

KK(AL)$_5$AKK;  (SEQ ID NO: 5)

(AL)$_6$AKK;  (SEQ ID NO: 6)

K(AL)$_6$AK;  (SEQ ID NO: 7)

K(AL)$_3$K(AL)$_2$K(AL)$_3$K; and  (SEQ ID NO: 9)

KK(AV)$_8$KK;  (SEQ ID NO: 8)

According to another embodiment, the amino acid pair repeats are consecutive or contiguous (i.e., adjacent to one another).

According to another embodiment, the peptide comprises or consists of the formula of $K_n(AX_1)_mX_2K_n$, wherein $X_1$ is Leucine (L) or Valine (V), $X_2$ is absent or Alanine (A), n, at each occurrence is independently 0-2 with the proviso that at least one terminal Lysine (K) is present, and m is 5-9. According to another embodiment, the peptide comprises or consists of the formula of $K_n(AL)_mAK_n$, wherein n, at each occurrence is independently 0-2 and m is 5-9. According to another embodiment, the peptide comprises or consists of the formula of $K_n(AV)_mK_n$, wherein n, at each occurrence is independently 0-2 with the proviso that at least one terminal Lysine (K) is present, and m is 6-9.

According to another embodiment, the peptide comprises or consists of the formula of $K_n(AL)_mK_n$, wherein n, at each occurrence is independently 0-2 with the proviso that at least one terminal Lysine (K) is present, and m is 6-9. According to an exemplary embodiment, the peptide comprises the amino acid sequence as set forth in KK(AL)$_8$KK (SEQ ID NO: 1). According to yet another exemplary embodiment, the peptide consists of the amino acid sequence as set forth in KK(AL)$_8$KK (SEQ ID NO: 1).

The term "peptide" as used herein encompasses native peptides (degradation products, synthetic peptides or recombinant peptides), peptidomimetics (typically including non peptide bonds or other synthetic modifications) and the peptide analogues peptoids and semipeptoids, and may have, for example, modifications rendering the peptides more stable while in the body or more capable of penetrating into cells. Peptides typically consist of a sequence of about 3 to about 50 amino acids. According to some embodiments, the peptide of the invention consists of at least 13 amino acids, at least 14 amino acids, at least 15 amino acids, at least 16 amino acids, at least 17 amino acids, at least 18 amino acids, at least 19 amino acids, or at least 20 amino acids. Each possibility represents a separate embodiment of the present invention.

According to additional embodiments, the peptide consists of at most 50 amino acids, at most 45 amino acids, at most 40 amino acids, at most 35 amino acids, at most 30 amino acids, at most 29 amino acids, at most 28 amino acids, at most 27 amino acids, at most 26 amino acids, at most 25 amino acids, at most 24 amino acids, at most 23 amino acids, at most 22 amino acids, at most 21 amino acids, at most 20 amino acids. Each possibility represents a separate embodiment of the present invention.

According to an exemplary embodiment, the peptide consists of 20 amino acids. According to yet another exemplary embodiment, the peptide consists of 15 amino acids. According to another embodiment, the peptide consists of 16 amino acids, 17 amino acids, 18 amino acids or 19 amino acids. Each possibility represents a separate embodiment of the present invention.

The terms "polypeptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "isolated" peptide refers to a peptide that is essentially free from contaminating cellular components, such as carbohydrate, lipid, or other proteinaceous impurities associated with the peptide in nature. Typically, a preparation of isolated peptide contains the peptide in a highly purified form, i.e., at least about 80% pure, at least about 90% pure, at least about 95% pure, greater than 95% pure, or greater than 99% pure. In another embodiment, the isolated peptide of the invention is a synthetic or recombinant peptide. In another embodiment, the isolated peptide of the invention is a synthetic peptide.

The present invention further provides fragments, analogs and chemical modifications of the peptides of the present invention as long as they show anti-inflammatory activity.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a Leucine (L) to Isoleucine (I). Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W) (see, e.g., Creighton, Proteins, 1984).

Thus, the term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another. Each possibility represents a separate embodiment of the present invention.

According to specific embodiments, an analog of the peptides of the present invention comprises a substitution of leucine with another hydrophobic residue such as isoleucine, valine, leucine or methionine. In a specific embodiment, at least one leucine is substituted with isoleucine.

According to specific embodiments, an analog of the peptides of the present invention comprises a substitution of lysine with another hydrophilic residue such as arginine, glutamine, asparagine, glycine or serine. In a specific embodiment, at least one lysine is substituted with arginine.

The phrase "conservative substitution" also includes the use of a chemically derivatized residue in place of a non-derivatized residue provided that such peptide displays the requisite function of modulating the immune system's innate response as specified herein.

Typically, the present invention encompasses derivatives of the peptides. The term "derivative" or "chemical derivative" includes any chemical derivative of the peptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-$NH_2$ acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —$CH_2$—NH—, —$CH_2$—S—, —$CH_2$—S=O, O=C—NH—, —$CH_2$—O—, —$CH_2$—$CH_2$—, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C—O—O—C(R)H—N); ketomethylene bonds (—CO—CH2-); α-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (MeAla), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide analogs, which can contain one or more D-isomer forms of the amino acids. Production of retro-inverso D-amino acid peptides where at least one amino acid, and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein.

According to a particular embodiment, the peptides of the present invention are diastereomeric peptides. The diastereomeric peptides are highly advantageous over all L- or all D-amino acid peptides having the same amino acid sequence because of their higher water solubility, lower immunogenicity (see, for example, Benkirane, N., et al., 1993, J. Biol. Chem. 268: 26279-26285), and lower susceptibility to proteolytic degradation. Such characteristics endow the diastereomeric peptides with higher efficacy and higher bioavailability than those of the all L or all D-amino acid peptides comprising the same amino acid sequence.

The term "diastereomeric peptide" as used herein refers to a peptide comprising both L-amino acid residues and D-amino acid residues. The number and position of D-amino acid residues in a diastereomeric peptide of the preset invention may be variable so long as the peptides are capable on modulating the immune system's innate response. In some embodiments, the peptides comprises at least 2 D-amino acid residues, at least 3 D-amino acid residues, at least 4 D-amino acid residues, at least 5 D-amino acid residues, at least 6 D-amino acid residues, at least 7 D-amino acid residues, at least 8 D-amino acid residues, at least 9 D-amino acid residues, wherein each possibility represents a separate embodiment of the invention.

Non-limiting examples of diasteriomeric peptides in accordance with the present invention include KKA LALALALALALALALALKK (SEQ ID NO: 10) and ALA LALALALALALALALKK (SEQ ID NO: 11) wherein L refers to D-Leucine.

The peptides of the invention may be synthesized or prepared by techniques well known in the art. The peptides can be synthesized by a solid phase peptide synthesis method of Merrifield (see J. Am. Chem. Soc., 85:2149, 1964). Alternatively, the peptides of the present invention can be synthesized using standard solution methods well known in the art (see, for example, Bodanszky, M., Principles of Peptide Synthesis, Springer-Verlag, 1984) or by any other method known in the art for peptide synthesis.

In general, these methods comprise sequential addition of one or more amino acids or suitably protected amino acids to a growing peptide chain bound to a suitable resin.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5dimethoxybenzyloxycarbonyl, o-nitrophenylsulfenyl, 2-cyano-t-butyloxycarbonyl, 9-fluorenylmethyloxycarbonyl (FMOC) and the like. The BOC or FMOC protecting group is preferred.

In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

The peptides of the invention may alternatively be synthesized such that one or more of the bonds, which link the amino acid residues of the peptides are non-peptide bonds. These alternative non-peptide bonds include, but are not limited to, imino, ester, hydrazide, semicarbazide, and azo bonds, which can be formed by reactions well known to skilled in the art.

The peptides of the present invention, analogs, or derivatives thereof produced by recombinant techniques can be purified so that the peptides will be substantially pure when administered to a subject. The term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

Included within the scope of the invention are peptide conjugates comprising the peptides of the present invention derivatives, or analogs thereof joined at their amino or carboxy-terminus or at one of the side chains via a peptide bond to an amino acid sequence of a different protein. Additionally or alternatively, the peptides of the present invention, derivatives, or analogs thereof can be joined to another moiety such as, for example, a fatty acid, a sugar moiety, arginine residues, hydrophobic moieties, and any known moiety that facilitate membrane or cell penetration. Conjugates comprising peptides of the invention and a protein can be made by protein synthesis, e.g., by use of a peptide synthesizer, or by ligating the appropriate nucleic acid sequences encoding the desired amino acid sequences to each other by methods known in the art, in the proper coding frame, and expressing the conjugate by methods commonly known in the art.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

Pharmaceutical Compositions of the Invention

According to another aspect, the present invention provides a pharmaceutical composition comprising as an active ingredient an isolated peptide of 13-35 amino acids comprising at least one Lysine residue and 5-9 repeats of an amino acid pair comprising Alanine and $X_1$, wherein $X_1$ is Leucine or Valine, and a pharmaceutically acceptable carrier.

The pharmaceutical compositions of the invention can be formulated in the form of a pharmaceutically acceptable salt of the peptides of the present invention or their analogs, or derivatives thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E.W. Martin, the contents of which are hereby incorporated by reference herein. Such compositions will contain a therapeutically effective amount of a peptide of the invention, preferably in a substantially purified form, together with a suitable amount of carrier so as to provide the form for proper administration to the subject.

The amount of the peptides of the present invention, which will be effective in the treatment of a particular disorder or condition will depend on the nature of the disorder or condition and on the particular peptide of the invention, and can be determined by standard clinical techniques known to a person skilled in the art. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Depending on the location of the tissue of interest, the peptides of the present invention can be supplied in any manner suitable for the provision of the peptide to cells within the tissue of interest. Thus, for example, a composition containing the peptides of the present invention can be introduced, for example, into the systemic circulation, which will distribute said peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

It may be desirable to administer the pharmaceutical composition of the invention locally to the area in need of treatment; this can be achieved by, for example, and not by way of limitation, local infusion, topical application, by injection, by means of a catheter, by means of a suppository, or by means of an implant, said implant being of a porous, non-porous, or gelatinous material. According to some preferred embodiments, administration can be by direct injection e.g., via a syringe, at the site of a damaged tissue.

For topical application, a peptide of the present invention, derivative, analog or a fragment thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as a fatty oil. In addition, dosage unit forms can contain various other materials which modify the physical form of the dosage unit, for example, coatings of sugar, shellac, or other enteric agents. The tablets of the invention can further be film coated.

The peptides of the present invention, derivatives, or analogs thereof can be delivered in a controlled release system. Thus, an infusion pump can be used to administer the peptide such as the one that is used, for example, for delivering insulin or chemotherapy to specific organs or tumors. In one embodiment, the peptide of the invention is administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

Use of the Peptides

The peptides of the present invention are capable of modulating the immune response for the treatment or prevention of an inflammatory condition, including but not limited to, microbial disease or disorder and allergic hypersensitivity conditions. The present invention further provides methods for overcoming endotoxin tolerance, and preventing or inhibiting endotoxin shock or sepsis.

Microbial Disease

The term "microbial" or the like includes but is not limited to organisms including bacteria, fungi, viruses, yeasts and/or moulds. In one embodiment, the microbial disease or disorder is a bacterial disease or disorder. In one embodiment the microbial infection is a bacterial infection. In another embodiment, the microbial disease is a microbial infection of the skin, lung, buccal cavity, gastro-intestinal tract, eye, ear, sinuses, kidney, mucosal surfaces, or urinary tract.

In another embodiment, the microbial disease or disorder is a skin disease or disorder or a tissue disease or disorder, such as psoriasis, acne, ulceration, wound infection or refractory wound(s), burn(s), dermatitis, athletes foot, and eczema. For example, the microbial disease or disorder is a bacterial infection, such as a bacterial infection of a wound, including an infection of any one or more of the following bacteria: *Staphylococcus aureus*, including methicillin-resistant *Staphylococcus aureus* (MRSA), *E. coli*, or *Pseudomonas aeruginosa*.

In another embodiment, the microbial disease or disorder is a lung disease or disorder, such as chronic obstructive pulmonary disease (COPD, also referred to as chronic obstructive respiratory disease (CORD)), tuberculosis, or emphysema. For example, the microbial disease or disorder is a bacterial infection of *Mycobacteria tuberculosis*, or *Mycobacteria paratuberculosis*.

In another embodiment, the microbial disease or disorder is an oral disease or disorder, such as dental caries, gingivitis, ulcers. For example, the microbial disease or disorder is a bacterial infection of any one or more of the following bacteria: *Streptococcus salivarius*, *S. mitis*, *S. mutans*, *S. rattus*, *S. cricetus*, *S. sobrinus*, *S. ferns*, *S. macacae*, or *S. downei*, *Lactobacillus* spp., including *Lactobacillus caseii*.

In one embodiment, the microbial disease or disorder is a gastro-intestinal disease or disorder, such as gastro-enteritis, ulcers including peptic ulcers, chronic gastritis, and duodenitis. For example, the microbial disease or disorder is a bacterial infection of any one or more of the following bacteria: *Helicobacter* spp., including *H. acinonychis*, *H. anseris*, *H. aurati*, *H. bilis*, *H. bizzozeronii*, *H. brantae*, *H. canadensis*, *H. canis*, *H. cholecystus*, *H. cinaedi*, *H. cynogastricus*, *H. felis*, *H. fennelliae*, *H. ganmani*, *H. hepaticus*, *H. mesocricetorum*, *H. marmotae*, *H. muridarum*, *H. mustelae*, *H. pametensis*, *H. pullorum*, *H. pylori*, *H. rappini*, *H. rodentium*, *H. salomonis*, *H. trogontum*, *H. typhlonius*, *H. winghamensis*, *Campylobacter* spp., including *C. coli*, *C. concisus*, *C. curvus*, *C. fetus*, *C. gracilis*, *C. helveticus*, *C. hominis*, *C. hyointestinalis*, *C. insulaenigrae*, *C. jejuni*, *C. lanienae*, *C. lari*, *C. mucosalis*, *C. rectus*, *C. showae*, *C. sputorum*, *C. upsaliensis*.

In another embodiment, the microbial disease or disorder is an eye disease or disorder, such as blepharitis, conjunctivitis, keratitis including fungal keratitis. For example, the microbial disease or disorder is a microbial infection of any one or more of the following microbes: *Staphylococcus* spp., *Aspergillus* fumigates, *Fusarium* spp. and *Candida* spp.

In another embodiment, the microbial disease or disorder is an ear or sinus disease or disorder, such as Otitis externa, Otitis media, sinusitis including acute sinusitis, chronic sinusitis and antibiotic-refractory chronic sinusitis. For example, the microbial disease or disorder is a microbial infection of the ear or sinus, including an infection of any one or more of the following microbes: *Staphylococcus* spp. including *Staphylococcus aureus*, *Pseudomonas aeruginosa*, *Aspergillus* spp., including *Aspergillus fumigates*, *Streptococcus* spp. including *Streptococcus pneumonia*, *Haemophilus influenza*, *Moraxella catarrhalis*, *Mycobacterium tuberculosis*, and *Candida* spp. including *Candida albicans*.

In various embodiments the microbial disease or disorder is, or the microbial infection is of any one or more of the following microbes: *Aspergillus* spp., including *Aspergillus flavus*, *Aspergillus fumigatus*, *Aspergillus niger*, *Bacillus* spp., including *Bacillus subtilis*, *Bacillus cereus*, *Boretella* spp., including *Boretella pertussis*, *Candida* spp., including *Candida albicans*, *Candida utilis*, *Chlamydophila* spp., including *Chlamydophila pneumoniae*, *Escherichia* spp., including *Escherichia coli*, *Haemophilus* spp., including *Haemophilus influenzae*, *Helicobacter* spp., including *Helicobacter pylori*, *Klebsiella* spp., including *Klebsiella pneumoniae*, *Listeria* spp., including *Listeria monocytogenes*, *Micrococcus* spp., including *Micrococcus fiavus*, *Moraxella* spp., including *Moraxella catarrhalis*, *Mycobacteria* spp., including *Mycobacteria tuberculosis*, *Mycobacteria paratuberculosis*, *Mycoplasma* spp., including *Mycoplasma pneumoniae*, *Pasteurella* spp., including *Pasteurella multocida*, *Penicillium* spp., including *Penicillium chrysogenum*, *Proteus* spp., including *Proteus mirabilis* and *Proteus vulgaris*, *Pseudomonas* spp., including *Pseudomonas aeruginosa/pyocyanea*, *Salmonella* spp., including *Salmonella typhi*, *Sarcinalutea* spp., *Serratia* spp., including *Serratia marcescens*, *Shigella* spp., including *Shigella boydii*, *Shigella fiexneri*, and *Shigella sonnei*, *Staphylococcus* spp., including *Staphylococcus albus*, and *Staphylococcus aureus* including methicillin-resistant *Staphylococcus aureus*, *Streptococcus* spp., including Group B Streptococci, *Streptococcus faecalis*, *Streptococcus pneumoniae*, and *Streptococcus pyogenes*, and *Vibrio* spp., including *Vibrio cholerae*.

In another embodiment, the microbial disease or disorder is a fungal disease or disorder. In another embodiment, the microbial disease is a yeast disease or disorder.

In various embodiments the microbial disease or disorder is, or the fungal infection is of any one or more of the following fungi: *Candida* spp., including *Candida albicans*, *Candida utilis*, *Aspergillus* spp., *Penicilliium* spp.

Sepsis

In a particular embodiment, the inflammatory condition is sepsis. Sepsis is defined as the presence or presumed presence of an infection accompanied by evidence of a systemic response called the systemic inflammatory response syndrome (SIRS). Sepsis is usually caused by bacterial infections (either Gram-negative or Gram-positive bacteria) but can also be caused by other pathogens. Most often however, sepsis is caused by Gram-negative bacteria infections. The injury and symptoms attributable to sepsis are not only caused by the bacteria but are also caused by a component of the bacteria cell wall known as endotoxin or LPS. LPS molecules are glycolipids that are ubiquitous in the outer membrane of Gram-negative bacteria. LPS is released when the immune system destroys the invading bacteria. The released LPS binds to monocytes, macrophages, and endothelial cells and triggers the production of various mediators such as TNF-α and interleukins (IL-1, IL-6, and IL-8). Production of excessive TNF-α, IL-1, IL-6, and IL-8 is a major cause of severe forms of sepsis.

In a particular embodiment of the invention, the inflammatory condition is Systemic inflammatory response syndrome (SIRS). SIRS is defined as the presence of two or more of the following: (1) temperature greater than 38° C. or less than 36° C.; (2) pulse rate greater than 90 beats/min; (3) respiratory rate greater than 20 breaths/min (or $PCO_2$ less than 32 torr); and (4) white blood cells count greater than $12000/mm^3$ or less than $4000/mm^3$, or greater than 10% immature band forms.

In another particular embodiment, the inflammatory condition is severe sepsis. Severe sepsis is defined as the sepsis which is accompanied by one or more organ dysfunctions. Organ dysfunction can be defined as acute lung injury; coagulation abnormalities; thrombocytopenia; altered mental status; renal, liver, or cardiac failure; or hypoperfusion with lactic acidosis.

In another particular embodiment, the inflammatory condition is septic shock. Septic shock is defined as the presence of sepsis and refractory hypotension, i.e., systolic blood pressure less than 90 mmHg, mean arterial pressure less than 65 mmHg, or a decrease of 40 mmHg in systolic blood pressure compared to baseline unresponsive to a crystalloid fluid challenge of 20 to 40 ml/kg. Thus, septic shock is effectively a form of severe sepsis.

Hypersensitivity

The pathological condition hypersensitivity is characterized by an excessive immune response to (an) allergen(s) resulting in gross tissue changes if the allergen is present in relatively large amounts or if the humoral and cellular immune state is at a heightened level. Physiological changes in anaphylactic hypersensitivity can include intense constriction of the bronchioles and bronchi of the lungs, contraction of smooth muscle and dilation of capillaries. Predisposition to this condition, however, appears to result from an interaction between genetic and environmental factors. Common environmental allergens which induce anaphylactic hypersensitivity are found in pollen, foods, house dust mites, animal danders, fungal spores and insect venoms. Atopic allergy is associated with anaphylactic hypersensitivity and includes the disorders, e.g., asthma, allergic rhinitis and conjunctivitis (hay fever), eczema, urticaria and very frequent are common are allergies to food constituents. However anaphylactic shock, a dangerous life-threatening condition anaphylaxis is usually provoked by insect stings or parental medication.

IgE-mediated allergies are triggered by binding of IgE to the high affinity IgE receptor (FcεRI), which is expressed on effector mast cells, basophils and activated eosinophils. As a result of these high affinity interactions, stable FcεRI:IgE complexes are displayed on the surface of effector cells. Exposure to allergens leads to cross-linking and eventually clustering of IgE:FcεRI complexes, thus triggering effector cell activation, degranulation and release of stored pro-allergenic mediators that lead to the initiation of an allergic response.

FcεRI is a tetramer made of one α chain, one β chain, and two identical, disulfide-linked γ chains 3. While rodent FcεRI has an obligatory αβγ2 tetrameric structure, human FcεRI can be expressed as both trimeric (αγ2) and tetrameric (αβγ2) structures. Rodent FcεRI is only expressed on mast cells and basophils whereas expression of human FcεRI extends to monocytes, eosinophils, platelets, Langerhans cells, and dendritic cells. In human antigen-presenting cells (Langerhans cells, monocytes, and dendritic cells) FcεRI is expressed as a trimeric complex, as opposed to the tetrameric structures prevalent in mast cells and basophils. While it is easy to induce local or systemic anaphylactic reactions in immunocompetent mice, these reactions are completely abolished in FcεRI-deficient mice. Therefore, FcεRI is indeed a crucial, key component in IgE-mediated allergic reactions (Kinet, 1999). The IgE binding site is located in the extracellular region of FcεRIα chain that consists of two extracellular Ig-like domains, a single transmembrane sequence and a cytoplasmic domain. The function of FcεRIβ-subunit, with its four transmembrane domains separating NH2- and COOH-terminal cytoplasmic tails, is to amplify cell activation signals with a gain factor ranging from 3 to 5 mediated through the FcεRIγ subunit. A possible association between various human FcεRIβ chain polymorphisms and atopic phenotypes has been suggested. Critical for receptor signaling, the two disulfide-linked γ-subunits are members of the γ/ζ/η family of antigen receptor subunits and consist essentially of a transmembrane region and cytoplasmic tail4. Both β and γ subunits are responsible for the downstream propagation of the signal through the phosphorylation of their immunoreceptor tyrosine-based activation motif (ITAM).

As used herein, the term "IgE-mediated disorder" means a condition, disorder or disease which is characterized by the overproduction and/or hypersensitivity to the immunoglobulin IgE. Non limiting examples of IgE-mediated disorders include conditions associated with anaphylactic hypersensitivity and atopic allergies, including for example: asthma, allergic rhinitis & conjunctivitis (hay fever), eczema, urticaria, food allergies and anaphylactic shock.

According to some embodiments, the allergic disorder is selected from the group consisting of: allergy-induced asthma, hypersensitivity, eczema conjunctivitis, urticaria, rhinorrhea, rhinitis gastroenteritis, pemphigus vulgaris, atopic dermatitis, eosinophilia, allergic bronchopulmonary aspergillosis, glomerular nephritis, parasitic diseases, interstitial cystitis, hyper-IgE syndrome, ataxia-telangiectasia, Wiskott-Aldrich syndrome, thymic alymphoplasia, Hodgkin's disease, IgE myeloma and graft-versus-host reaction. Each possibility is a separate embodiment of the present invention.

The following examples are presented in order to more fully illustrate some embodiments of the invention. They should, in no way be construed, however, as limiting the broad scope of the invention.

EXAMPLES

Materials and Methods

Peptide Synthesis and Purification.

Peptides were synthesized by a 9-fluorenylmethoxylcarbonyl (Fmoc) solid-phase method on Rink amide MBHA resin (Calbiochem-novabiochem, San Diego, Calif.) by using an ABI 433A automatic peptide synthesizer (Applied Biosystems, Foster City, Calif.). Peptide synthesis was followed by peptide cleavage from the resin by incubation for 3 h with 95% TFA, 2.5% $H_2O$, and 2.5% triethylsilane. Purification of the crude peptide was performed by RP-HPLC (>98%) on a Vydac C4 column (Grace Discovery Sciences, Deerfield, Il). The peptides were identified by electrospray mass spectroscopy.

Cell Culture.

All in vitro assays were performed on RAW264.7 murine macrophages (ATCC-TIB71). Cells were grown in DMEM supplemented with 10% FBS, L-glutamine, sodium pyruvate, non-essential amino acids and antibiotics (Biological Industries, Beit Haemek, Israel). Incubator was set on 37° C. with a humidified atmosphere containing 5% $CO_2$.

XTT Cytotoxicity Assays.

$1\times10^4$ cells per well were grown overnight on a 96-well plate. The following day, the media were replaced with 90 µl fresh culture medium and 10 µl solution buffer containing different concentrations of the different peptides. Peptide concentrations ranged from 0.78-100 µM. The cells were then incubated for 2 hours before adding to each well 50 µl of 2,3-bis-2H-tetrazolium-5-carboxanilide inner salt (XTT) reaction solution (Biological Industries). Viability was determined as described previously (Makovitzki et al. Cancer Res 69, 3458-63, 2009; Papo et al. 2006). The $LC_{50}$ (the concentration at which 50% of the cells die) for each peptide was obtained from the dose-dependent cell viability curves.

TNFα Secretion by RAW264.7 in Response to TLR Activation.

$2\times10^5$ cells per well were cultured overnight in a 96-wells plate. The following day, the media were replaced by fresh DMEM, including all supplements. Peptides were dissolved in DMSO and added to the cells in different concentrations. Final concentration of DMSO was 1% for all groups. Cells were incubated with the peptide for 2 hours, then LPS (TLR4 activator) or LTA (TLR2 activator) was added to the cells at 10 ng/ml or 500 ng/ml, respectively. The cells were further incubated for 5 hrs at 37° C., after which samples of the media from each treatment were collected and stored at −20° C. TNFα concentration in each sample was evaluated using a mouse TNFα enzyme-linked immunosorbent assay kit (Biosource™ ELISA, Invitorgen), according to the manufacturer's protocol. All experiments were done in triplicates.

Fluorescent Labeling of Peptides.

The following fluorophores were used for fluorescent labeling: 4-Fluoro-7-nitrobenzofurazan (NBD, Bio-Chemika), and 5(6)-carboxytetramethylrhodamine N-succinimidyl ester (TAMRA, BioChemika). Resin-bound peptides were treated with each of the listed fluorophores dissolved in dimethyl formamide (DMF), leading to the formation of resin-bound N-terminal fluorophore peptides. 2% DIEA was added to the TAMRA solution. Incubation was done for 1 hr (NBD) or overnight (TAMRA). Following the incubation, the resin was washed thoroughly with DMF and then with methylene chloride, dried under nitrogen flow, and then cleaved and purified as described above.

LPS Binding Assays.

NBD-labeled peptides (50 µl, 2 µM, PBS$^{-/-}$ 2% DMSO) were added to different concentrations of LPS (50 µl PBS$^{-/-}$) in a opaque black 96 well plate. After 10 minutes of incubation at room temperature, the fluorescence was measured using an excitation of 467 nm and emission of 530 nm. The data were plotted and Kd and Bmax values obtained using NLLSQ analysis.

Oligomerization Assays. Rhodamine-labeled peptides were dissolved in DMSO, added to 400 µl of PBS$^{-/-}$ solution and brought to equilibrium (peptide's final concentration 0.1 µM, DMSO 0.25% v/v). Changes in the intensity of the fluorescence emission were followed after the addition of purified LPS until the system regained equilibrium. At the final stage proteinase-K (Sigma Aldrich) was added to the system and the increase in the emission of the rhodamine conjugated peptide was monitored. Excitation wavelength was set at 530 nm and emission at 580 nm, and the final concentration of proteinase-K was 62.5 µg/ml. An increase in fluorescence indicates that the peptide exists as an oligomer (Papo, 2002). All fluorescence measurements were performed at 25° C.

Antimicrobial Assays.

The antibacterial activity of the peptides was examined in sterile 96-well plates (Nunc F96 microtiter plates) in a final volume of 100 µl, as follows. Aliquots (50 µl) of a suspension containing bacteria at a concentration of $10^6$ colony-forming units/ml in culture medium (LB medium) were added to 50 µl of peptide serially diluted in culture medium (100 µM-0.78 µM). Inhibition of growth was determined by eye after an incubation of 18-20 h at 37° C. Antibacterial activities were expressed as the minimal inhibitory concentration, the concentration at which 100% inhibition of growth was observed after 18-20 h of incubation. In these the effect of the peptides on *E. coli* (ATCC:25922) and *S. aureus* (ATCC:6538P) was tested. Notably, *E. coli* and *S. aureus* are representatives of both Gram negative and Gram positive bacteria, respectively.

Circular Dichroism (CD) Spectroscopy.

CD measurements were performed on an Aviv 202 spectropolarimeter (Applied Photophysics spectropolarimeter, United Kingdom). The spectra were scanned using a thermostatic quartz cuvette with a path length of 1 mm. All measurements were done at 25° C. The average time recording of each spectrum was 20 seconds in 1 nm steps in the wavelength range of 190-260 nm. The peptides were scanned at a concentration of 50 µM in DDW with or without 50 µM of purified *E. coli* LPS (Sigma Aldrich). Average MW of LPS used for calculations is 4 kD.

In Vivo Studies.

Animal studies were carried out in strict accordance to the Israeli law and the National Research Council guidelines (Guide for the Care and Use of Laboratory Animals 2010). All animal experiments were conducted at the Weizmann Institute of Science and approved by the Weizmann Institutional Animal Care and Use Committee.

Toxicity was tested by intraperitoneal injection of $K_2(AL)_8K_2$ (100 mg/kg in 400 µl saline) in female C57B1 mice (n=2). Mice were continuously observed for 1 hour immediately following injection and once per day for 7 days. To examine the effect of our peptides on acute septic shock driven by LPS hyperactivation of TLR4 we have used murine models as described before (Zheng et al. Int Immunopharmacol 10, 1209-19, 2010; Arima et al, 2005). Briefly, 12 weeks old C57 Black female mice were treated with 100 ng of LPS injected IP in a saline solution (200 µl, pH 6.5) containing 200 mg/ml of D-galactosamine (Calbiochem). Treated mice received one IP injection of 10 mg/kg peptide dissolved in saline (200 µl) following the LPS injection. In the second model heat-killed bacteria were used to induce a lethal septic shock. *E. coli* cells were grown to a mid log phase (OD=0.5) at 37° C., cooled on ice, and centrifuged at 3500 rpm for 10 minutes at 4° C. The cells were re-suspended in saline for a concentration of $2\times10^9$ cells in 200 µl and heated at 95° C. for 30 minutes. Each animal received an IP injection of 2×109 cells in 200 µl saline followed by injection of 10 mg/kg peptide dissolved in saline (200 µl). Animals were monitored for survival and for signs of sepsis for the next 14 days after LPS injection. Peptides used as the acetic acid salts for in vivo experiments. For LPS driven septic shock n=8, for heat killed bacteria n=11. Experiments were done according to the regulations of animal care facility at the Weizmann Institute of Science.

Example 1

20-Mer Hydrophobic Peptides with 2 Lysine Residues on Each Terminus are Potent LPS and LTA Neutralizers Initially the inventors designed hydrophobic peptides composed of 8 alanine-leucine (AL) or alanine-valine (AV) repeats and 4 lysine residues, 2 on each terminus (Table 1).

TABLE 1

20 mer peptides composed of alanine-leucine, alanine-valine or alanine-alanine repeats with 4 flanking lysines

| Name | Calculated hydrophobicity* | HPLC RT** |
|---|---|---|
| $K_2(AL)_8K_2$ (SEQ ID NO: 1) | 1.46 | 27 |
| $K_2(AV)_8K_2$ (SEQ ID NO: 8) | 1.48 | 24 |
| $K_2(AA)_8K_2$ (SEQ ID NO: 12) | 0.66 | 15 |

*Calculated hydrophobicity is obtained from the Expasy server, measured using the GRAVY index,
**HPLC retention time (RT) represents time for elution in minutes on a C4 column with a gradient of 10-90% ACN in 40 minutes.

Figure 1B:
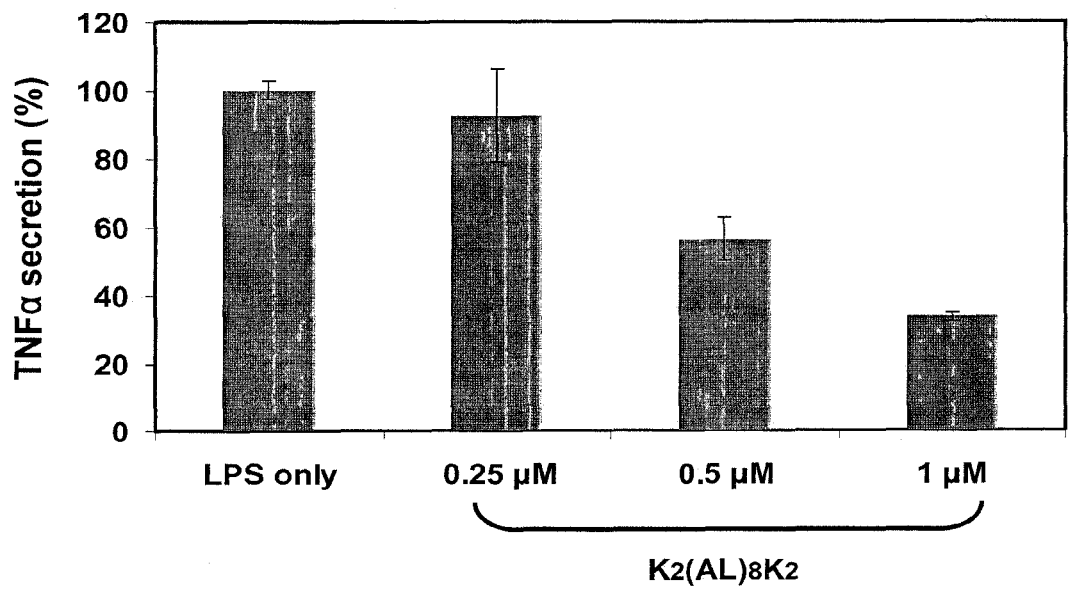
FIG. 1B shows dose dependent inhibition of TNFα secretion by $K_2(AL)_8K_2$.

The peptides were tested for their ability to inhibit TLR4 and TLR2 activation by LPS and LTA, respectively. The results show that the $K_2(AL)_8K_2$ (SEQ ID NO:1) peptide is highly potent in inhibiting LPS and LTA activation of the macrophages. The $K_2(AV)_8K_2$ (SEQ ID NO:8) peptide showed good inhibition for LTA activation but only medium inhibition for LPS activation (FIG. 1A). Therefore, the $K_2(AL)_8K_2$ peptide was examined further, and a dose dependent inhibition of macrophage activation was observed, showing a potent activity of ~50% inhibition at a low peptide concentration of 500 nM (FIG. 1B). In comparison, at a concentration of 20 µM, a less hydrophobic peptide analog peptide composed of 16 alanines and 2 lysines did not inhibit macrophage activation.

Example 2

Peptide Length, Charge, and Charge Distribution Affect LPS Neutralization, Antimicrobial Activity and Toxicity Next, the inventors tested which parameters are important for activity based on the most active LPS neutralizer ($K_2(AL)_8K_2$). To this end, various peptides were synthesized wherein their length, charge and charge position were systematically varied, and their ability to inhibit TLR4 activation was tested (Table 2).

TABLE 2

Model peptides synthesized with different charges, length, sequence order, and mixed D-L amino acids (D-amino acid are underlined).

| Formula | Sequence | SEQ ID NO |
|---|---|---|
| $K_2(AL)_8K_2$ | KKALALALALALALALALKK | 1 |
| $(AL)_9K_2$ | ALALALALALALALALALKK | 2 |
| $K(AL)_9K$ | KALALALALALALALALALK | 3 |
| $L(AL)_9K$ | LALALALALALALALALALK | 13 |
| $4D-K_2(AL)_8K_2$ | KKA_L_ALA_L_ALALA_L_ALA_L_AKK | 14 |
| $4D-(AL)_9K_2$ | ALA_L_ALA_L_ALALA_L_ALA_L_AKK | 15 |
| $K(AL)_3K(AL)_2K(AL)_3K$ | KALALALKALALKALALALK | 9 |
| $K_2(AL)_5AK_2$ | KKALALALALALAKK | 5 |
| $K_2(AL)_3K_2$ | KKALALALKK | 16 |

Figure 2A:
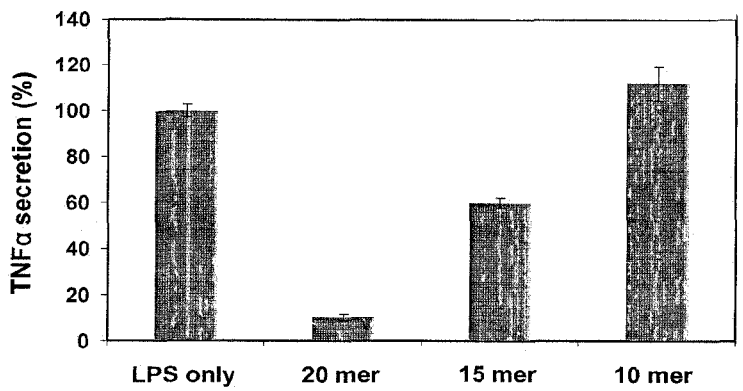
FIGS. 2A-2C demonstrate peptide inhibition of TNFα secretion upon stimulation of RAW264.7 macrophages with LPS.

The effect of the peptide's length (20, 15 and 10 mer) on peptides with a specific charge (+5) was examined. The 20 mer gave a strong, concentration dependent inhibition of TNFα (FIG. 2A). The 15 mer gave a lower inhibition and the 10 mer was not active up to a concentration of 20 µM.

Figure 2B:
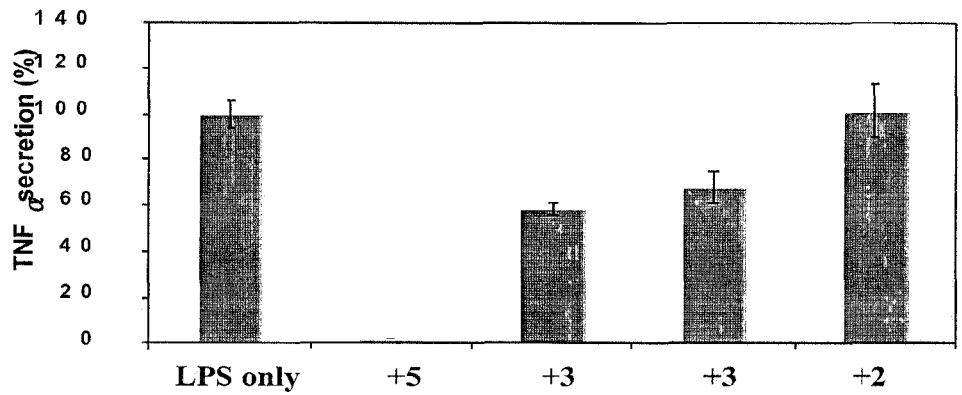

The net charge of the peptides was also observed to play a role in LPS neutralization. Testing peptides with a set length (20 mer) with different charges (+5, +3 and +2) showed that +5 was the most active in TLR4 inhibition, +3 gave medium activity and +2 did not show any activity (FIG. 2B). Notably, the exact arrangement of the charges on the termini did not affect this property as two different peptides with (+3) gave the same activity.

Figure 2C:
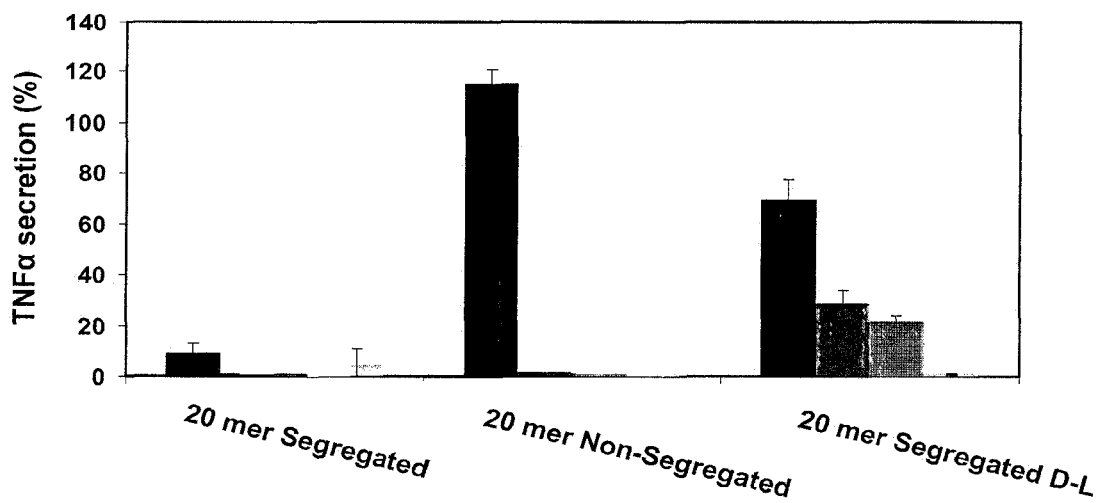

Finally, D amino acid substitution and charge distribution on the peptide activity was tested. The results reveal that a peptide that incorporated 4 D-leucine residues was not as active as the parental $K_2(AL)_8K_2$ peptide. Also, a peptide with an evenly distributed charge lost the ability to some extent to neutralize LPS (FIG. 2C). Most importantly, this peptide showed antimicrobial activity against both Gram positive and Gram negative bacteria, and high toxicity against RAW264.7 macrophages (Table 3).

TABLE 3

Antimicrobial activity against Gram-positive and Gram-negative bacteria expressed as the minimum inhibitory concentration (MIC). Toxicity measured (IC50) against RAW264.7 macrophages.

| Peptide | E. coli 25922 (µM) | S. aureus 6538P (µM) | IC$_{50}$ macrophages RAW264.7 (µM) |
|---|---|---|---|
| $K_2(AV)_8K_2$ (SEQ ID NO: 8) | >100 | >100 | 90 |
| $K_2(AL)_8K_2$ (SEQ ID NO: 1) | >100 | >100 | >100 |
| $(AL)_9K_2$ (SEQ ID NO: 2) | >100 | >100 | >100 |
| $K(AL)_9K$ (SEQ ID NO: 3) | >100 | >100 | >100 |
| $L(AL)_9K$ (SEQ ID NO: 13) | >100 | >100 | >100 |
| $4D-K_2(AL)_8K_2$ (SEQ ID NO: 14) | 100 | 100 | >100 |
| $4D-(AL)_9K_2$ (SEQ ID NO: 15) | >100 | >100 | 50 |
| $K(AL)_3K(AL)_2K(AL)_3K$ (SEQ ID NO: 9) | 25 | 12.5 | 25 |
| $K_2(AL)_5AK_2$ (SEQ ID NO: 5) | >100 | >100 | >100 |
| $(AL)_6AK_2$ (SEQ ID NO: 6) | >100 | >100 | >100 |
| $K(AL)_6AK$ (SEQ ID NO: 7) | >100 | >100 | >100 |
| $(AL)_7K$ (SEQ ID NO: 4) | >100 | >100 | >100 |
| $K_2(AL)_3K_2$ (SEQ ID NO: 16) | >100 | >100 | >100 |

Example 3

Figure 3A:
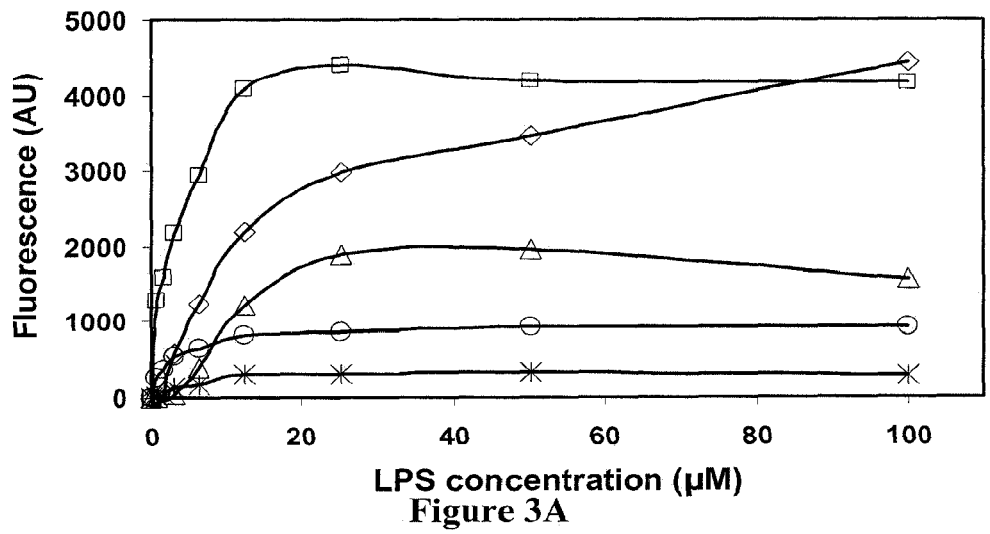
FIGS. 3A-3C demonstrate high LPS affinity and a different oligomerization state in peptides that neutralize LPS.

High LPS Affinity and a High Oligomerization State Observed in Peptides that Neutralize LPS In order to examine possible mechanisms of action for LPS neutralization, the affinity of the different peptides towards LPS was measured. NBD emission is sensitive to changes in the proximal hydrophobic environment. LPS was titrated to a solution of NBD conjugated peptides, and the increase in the fluorescence emission was measured (FIG. 3A). The peptides affinity for LPS ranged from $K_d$=2.6 µM, for the most active peptide $K_2(AL)_8K_2$ to $K_d$=10-15 µM for the inactive peptide $K_2(AL)_3K_2$ The relatively small differences in the affinities of the different peptides towards LPS suggest that LPS binding is not the sole determinant of detoxification. For example $K_2(AL)_5AK_2$ with $K_d=2.7$ μM showed only 50% inhibition at 20 μM whereas similarly binding $K_2(AL)_8K_2$ showed 90% inhibition at the same concentration. Closer examination of the LPS titration curves revealed that the values of Bmax were different for these peptides (Table 4). This may reflect the oligomerization state of the peptide when bound to LPS. Quenching of the fluorescent signal due to a highly oligomerized peptide resulted in a lower Bmax.

Thereafter, the oligomerization state of representative peptides was tested in the presence of LPS using rhodamine labeled peptides. Rhodamine fluorescence does not depend on the hydrophobicity of its surrounding, enabling the discrimination between hydrophobic (surrounding) effects and oligomerization effects. Two representative peptides with low, medium and high Bmax values were used for this experiment.

Figure 3B:
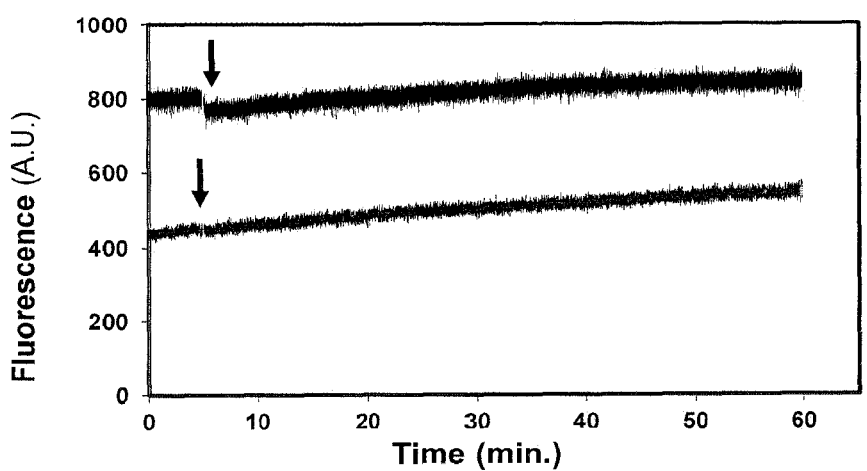
Figure 3C:
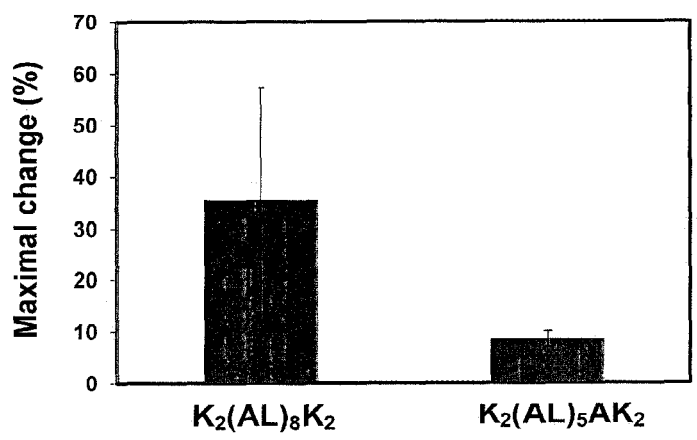
Figure 4A:
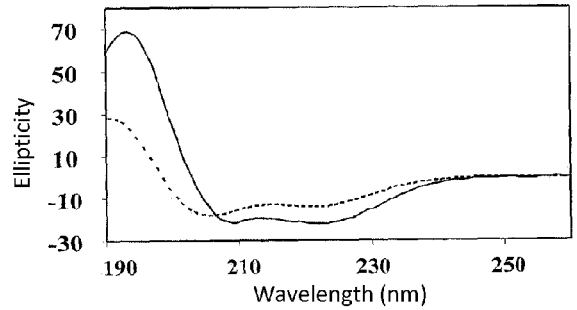
FIGS. 4A-4E shows CD measurements with selected peptides with (solid lines) and without LPS (dotted lines). Measurements performed in DDW with peptides and LPS concentration of 50 μM.
Figure 4D:
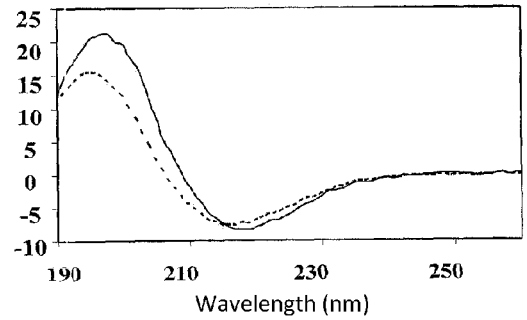
Figure 4B:
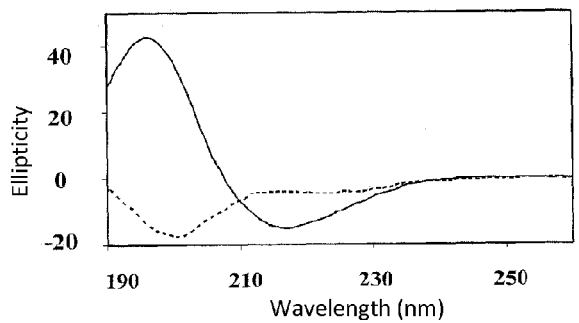
Figure 4E:
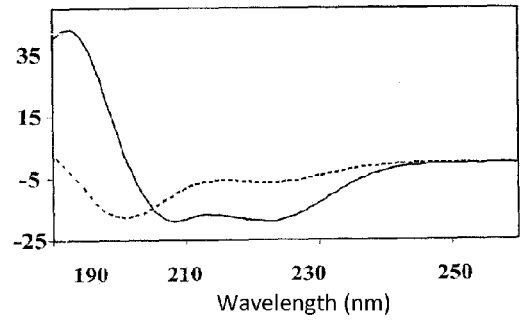
Figure 4C:
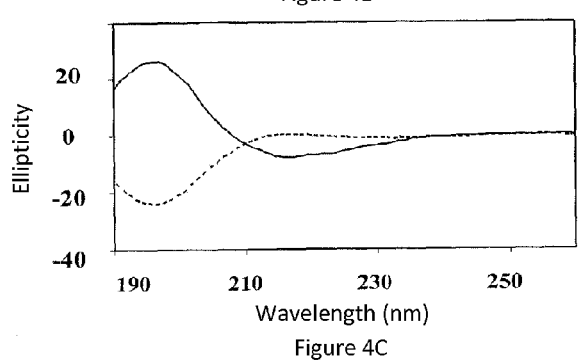

As seen in FIG. 3B, $K_2(AL_8)K_2$ (Right panel, grey line), a highly active peptide with relatively low Bmax aggregates in the presence of LPS, whereas $K_2(AL_5)AK_2$ (Right panel, black line) a peptide with a very high Bmax does not aggregate under the same conditions.

The differences in the aggregation are reflected by both the initial fluorescence of the peptide (the lower the initial fluorescence, the higher is the aggregation state) as well as maximum recovery of the fluorescence at the end of the experiment. This data shows that $K_2(AL_6)K_2$ has a maximum change in fluorescence of 35.6±21.7 (n=3), whereas $K_2(AL_5)AK_2$ shows only 8.6±1.5 (n=2).

TABLE 4

NBD-labeled peptide affinity to LPS, with Bmax as an indication of the final oligomerization state.

| Peptide | Kd (μM) | Bmax (A.U.) |
|---|---|---|
| $K_2(AL)_8K_2$ (SEQ ID NO: 1) | 2.6 | 982 |
| 4D-$K_2(AL)_8K_2$ (SEQ ID NO: 14) | 15.6 | 4678 |
| $K(AL)_3K(AL)_2K(AL)_3K$ (SEQ ID NO: 9) | 9.6 | 1810 |
| $(AL)_9K_2$ (SEQ ID NO: 2) | 4.4 | 312 |
| $K_2(AL)_5AK_2$ (SEQ ID NO: 5) | 2.7 | 4517 |

Example 4

Secondary Structure of Neutralizing Peptides is Enhanced in LPS Environment

To test the effect of LPS on the structure of the different peptides, circular dichroism (CD) was performed with and without LPS. LPS enhanced the structure of the peptides or even induced a structure for some of the peptides. For example, the peptide $K_2(AL)_5AK_2$ exhibited a random coil structure in solution but adopted a β-sheet structure in the presence of LPS. Interestingly, the peptides adopted both α-helix and β-sheet structures suggesting that a specific structure is not a prerequisite for LPS neutralization (FIG. 4). On the other hand, selected examples suggest that peptides with α-helical structure are more active than those with a β-sheet structure: while $K_2(AL)_8K_2$ and $K(AL)_3K(AL)_2K(AL)_3K$ are highly active and adopt an α-helical structure in LPS, $K_2(AL)_5AK_2$ and $K_2(AV)_8K_2$ show lower activity and adopt a β-sheet conformation upon interaction with LPS.

The CD analysis can also be used to confirm the oligomerization states that were observed in other experiments. Measuring the ratio between 222/208 serves as an indication for the oligomerization state of the peptides, where values of ~0.8 indicate a monomer and values ~1 and higher indicate an oligomeric state (Wexler-Cohen et al. Biochemistry 44, 5853-61, 2005). It is now revealed that $K_2(AL)_8K_2$, the most active peptide, moved from a monomeric state in solution (222/208=0.82) to an oligomeric state upon interaction with LPS (222/208=1.05). $K(AL)_3K(AL)_2K(AL)_3K$ also showed an oligomeric state in LPS (222/208=1.00). These results are in agreement with the NBD binding assays, strengthening the idea that LPS mediated oligomerization is a key feature for neutralization activity.

Example 5

The $K_2(AL)_8K_2$ Peptide Inhibits Severe Septic Shock Development in Mice in Two Different Models Efficacy testing was performed in two different animal models of septic shock. In the first model, sepsis was induced by injection of purified LPS, whereas in the second model heat killed bacteria were used. The $K_2(AL)_8K_2$ was chosen since this peptide exhibited the most desirable LPS neutralization properties: It inhibited TNFα secretion in stimulated macrophages at a nanomolar concentration, it had a strong binding affinity to LPS, and it was non-toxic to cultured macrophages.

Initially, this peptide was tested for toxicity in vivo using C57BL mice and at the highest dose tested (100 mg/kg i.p.), no lasting adverse effects were observed. At 30 minutes post injection, mice appeared and behaved normally.

Figure 5A:
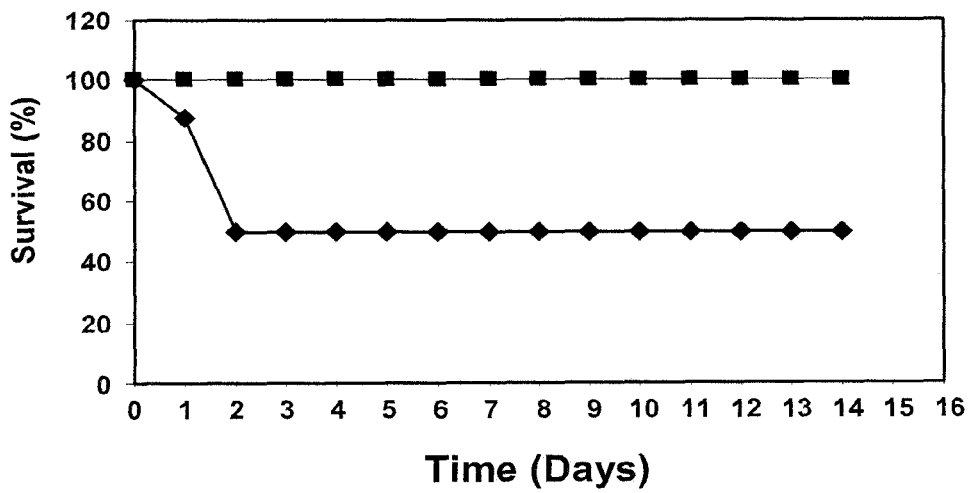
FIGS. 5A-5C show the peptide $(K_2(AL)_8K_2)$ affect on protection from sepsis. Sepsis was induced in C57BL mice by i.p. injection of purified LPS (100 ng) with D-galactosamine (40 mg) in 200 μL saline, n=8 (FIG. 5A) or heat killed *E. coli* ($2\times10^9$ CFU, in 200 μL saline) n=11 (FIG. 5B). Treatment was administered immediately following sepsis induction with 200 μL i.p. injection of $K_2(AL)_8K_2$ (10 mg/kg) (v), or saline control (υ).

For the first sepsis challenge (FIG. 5A, upper panel) C57BL mice were injected i.p. with 100 ng purified LPS (*E. coli* strain 0111:B4) and D-galactosamine (40 mg), and were either treated or untreated with the $K_2(AL)_8K_2$ peptide. In the untreated group (LPS challenge and saline only), 50% mortality was observed within 24 hours. A single i.p. injection of the peptide (10 mg/kg) immediately after the challenge resulted in complete protection of the mice: 100% survival (FIG. 5A).

Figure 5B:
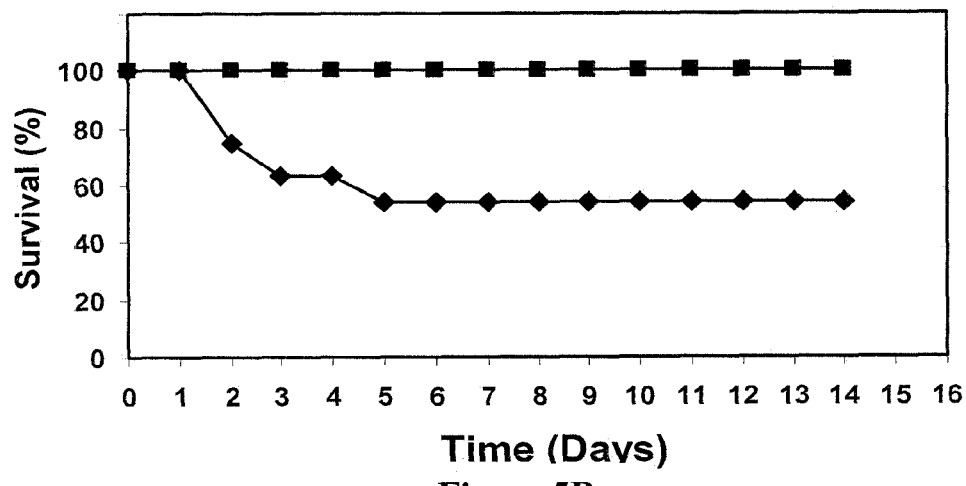

A second model with heat killed *E. coli* was performed as well (FIG. 5B). Only 55% of the untreated mice survived (heat killed *E. coli* and saline) while the treated mice (heat killed *E. coli* followed by injection of $K_2(AL)_8K_2$, 10 mg/kg) exhibited 100% recovery.

Figure 5C:
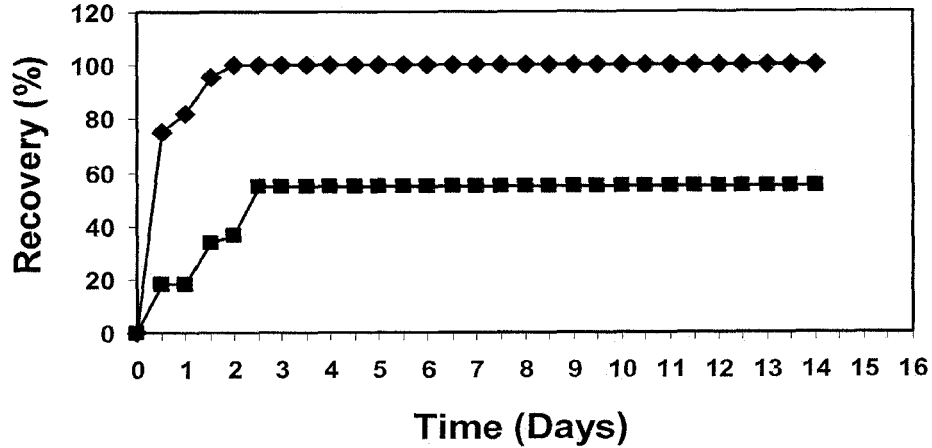

In addition the recovery of the mice during the first 4 days was closely monitored until no signs of sepsis were observed. Twice per day each mouse was scored on three physical signs of sepsis: low motility, shivering, and puss secretion from the eyes. The recovery time for animals treated with the peptide was significantly shorter than that of the untreated animals (FIG. 5C).

Example 6

In Vitro FceRI-Mediated Degranulation Studies

In order to study the specific effect of the peptides of the invention on direct IgE mediated degranulation, the rat basophilic cell line (RBL-2H3) was used. This cell line expresses high levels of surface IgE receptor that binds IgE with high affinity (FceRI). Upon adding an allergen (IgE antigen) there is a cross-linking of adjacent FcεRs that results in degranulation and release of histamine. Degranulation was measured as release of intracellular β-hexoseaminidase (Nunomura et al., Int Immunol 17, 685-94, 2005).

In this assay system, RBL cells were incubated with the DNP-specific murine monoclonal IgE SPE7 (Eshhar et al., J Immunol 124:775, 1980) for 2.5 hours. The cells were washed and centrifuged and then further incubated with the DNP-BSA antigen that crossed-link the FcεRI bound IgE. Next, extracellular hexoseaminidase levels were evaluated by their ability to hydrolyze the 4-nitrophenyl-N-acetyl-β-D-glucosaminide substrate which results in the accumulation of a colored product. The tested peptides (see Table 5) were added at different concentrations and stages of the assay and tested for their ability to inhibit this reaction.

In the first set of experiments, RBLs were incubated with different concentrations of the $(AL)_6AK_2$ peptide or irrelevant control peptide (alpha subunit peptide) in the presence of IgE. Following incubation, the cells were washed and $DNP_{10}$-BSA with peptide was added to crosslink adjacent FcεRI (FIG. 6). Following incubation, the cells were washed and suspended in the degranulation medium for either 30 (FIG. 6A) or 60 min. (FIG. 6B). Similar concentration dependent inhibition patterns were obtained after 30 and 60 minutes.

TABLE 5 peptide sequences and designations.

| Formula | Sequence | SEQ ID NO |
|---|---|---|
| $K_2(AL)_8K_2$ | KKALALALALALALALALKK | 1 |
| $(AL)_9K_2$ | ALALALALALALALALALKK | 2 |
| $L(AL)_9K$ | LALALALALALALALALALK | 13 |
| $(AL)_6AK_2$ | ALALALALALALAKK | 6 |
| $K_2(AL)_{10}AK_2$ | KKALALALALALALALALALAKK | 17 |

In another set of experiments, crosslinking the FcεRI was achieved by a different method. In this experimental setting, RBLs were incubated with rat anti-FcεRI monoclonal antibody (EM51.2, diluted to cause 70% degranulation) in the presence of different concentrations of $(AL)_6AK_2$ peptide. FIG. 7 shows that in this model, the peptide was able to inhibit degranulation in a dose dependent manner with 50% maximal inhibition (FIG. 7A). The negative control TAR-1, an unrelated peptide, did not show any inhibition. As in FIG. 1, doubling the degranulation time (60 min.) showed the same profile of inhibition (FIG. 7B).

Figure 8:
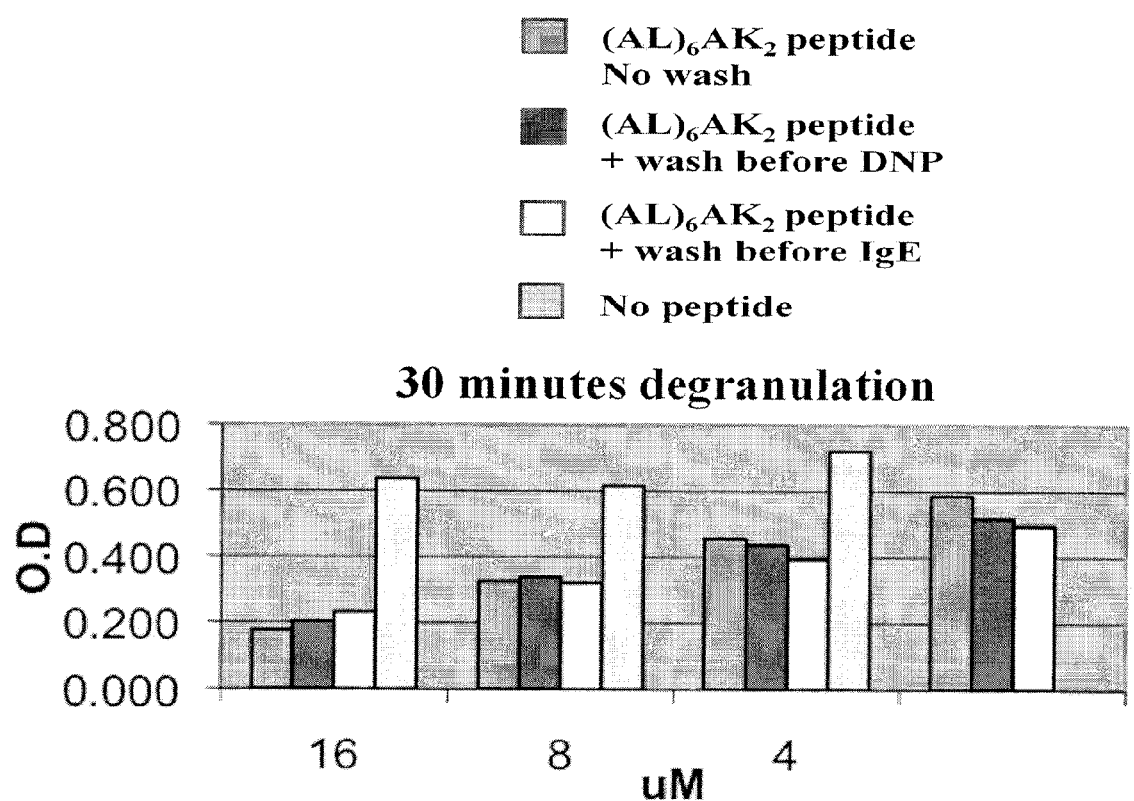
FIG. 8 shows that removal of $(AL)_6AK_2$ peptide before degranulation does not decrease its inhibitory capacity. Degranulation was performed as described below, by adding the $(AL)_6AK_2$ peptide, TNP-specific IgE and the DNP-BSA (allergen) without washing during the incubation period. In the other groups RBL cells were washed in different stages: after adding the peptide and before adding DNP-BSA or before adding IgE or without peptide.

Incubation of RBLs with the $(AL)_6AK_2$ peptide only, at the first stage before adding the antigen or anti FcεRI, was sufficient to inhibit the degranulation. This control is of major importance to ensure that the peptide does not interact with the DNP-BSA itself. As shown in FIG. 8, the peptide inhibited degranulation, regardless of the assay steps. Although its presence through all the steps gave the highest degree of inhibition, subsequent washes between the assay steps did not significantly decrease the degree of inhibition. In addition, the $(AL)_6AK_2$ peptide as well as the other peptides used in the study did not kill or inhibited the growth of the RBL cells in all the concentrations used in this study (XTT assay, data not shown).

Figure 9:
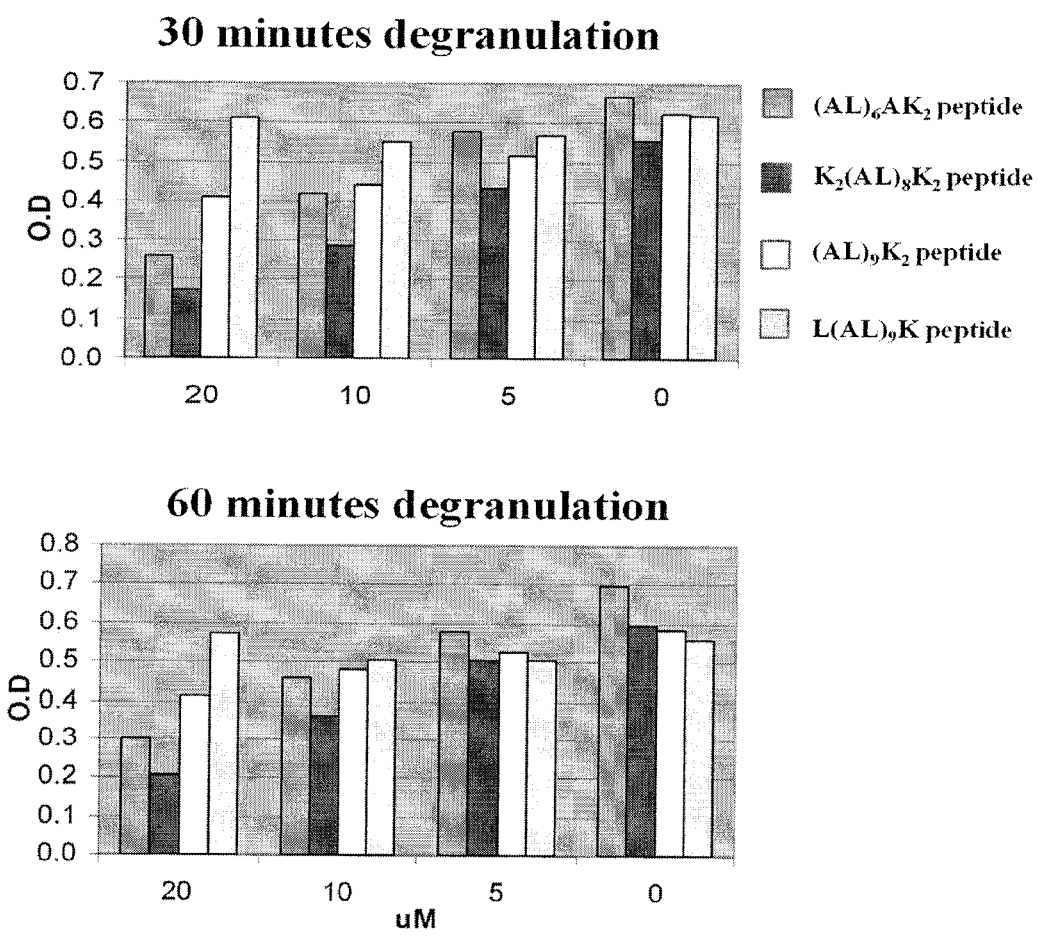
FIG. 9 is a comparison of the degranulation inhibitory capacity of different $K_n(L)_8K_2$ peptides. Degranulation of RBL was performed by cross-linking of FcεRI by IgE and DNP-BSA in the presence of peptides of the invention.

In an additional set of in vitro experiments, different peptides composed of alanine leucine and lysine at various lengths were tested. The most active peptide, $K_2(AL)_8K_2$ showed a maximum inhibition of 70% whereas a similar peptide ($L(AL)_9K$) with only one lysine gave no inhibition (FIG. 9).

TABLE 6

Peptide inhibitory effects on RBL degranulation (derived from FIG. 9A, peptide concentration 20 μM)

| Peptide | Inhibition of Degranulation (%) |
|---|---|
| $K_2(AL)_8K_2$ (SEQ ID NO: 1) | 70 |
| $(AL)_9K_2$ (SEQ ID NO: 2) | 30 |
| $L(AL)_9K$ (SEQ ID NO: 13) | 0 |
| $(AL)_6AK_2$ (SEQ ID NO: 6) | 50 |

To summarize the in vitro results, various peptides tested inhibited degranulation in the in vitro RBL model. The inhibition was seen in two different modes of degraulation (by IgE and allergen and by anti-FcεRI) suggesting that it is not dependent on the mode of triggering of the mast cell high affinity receptor-mediated degraulation. This rules out the possibility that the inhibition was due to an indirect interaction of the peptide with DNP-BSA antigen. According to the presented results, it is clear that there is a minimum number of charged lysine residues that are essential for the inhibitory activity as a peptide with a single charge gave no inhibition. In addition, the inhibitory activity increases with the number of terminal flanking lysines.

Example 7

The $K_2(AL)_8K_2$ Peptide Inhibits Passive Cutaneous Anaphylaxis (PCA)

Figure 10:
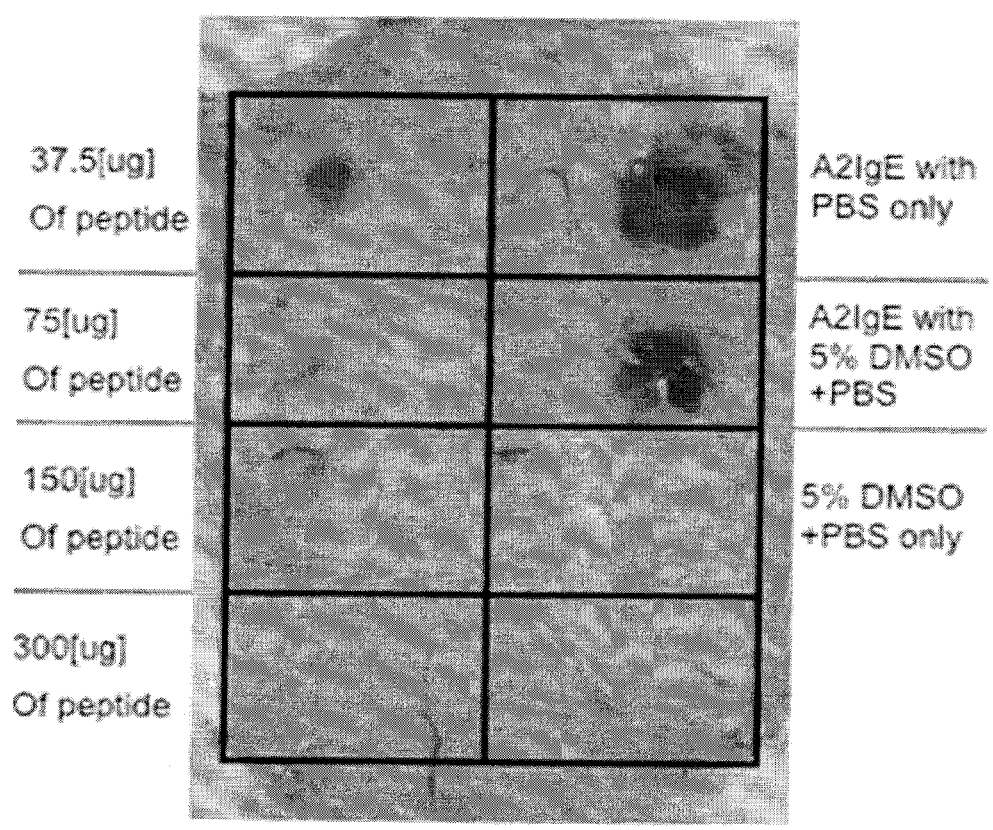
FIG. 10 shows inhibition of passive cutaneous anaphylaxis (PCA) by the $K_2(AL)_8K_2$ peptide. DNP-specific IgE SPE-7 (Sigma A2IgE) was injected i.d. to shaved back of anesthetized Lewis rat either with PBS (upper right flank) or 5% DMSO without ($2^{nd}$ right) or with different amounts of the $K_2(AL)_8K_2$ peptide (left flank, in increasing amounts). Thirty minutes later, the rat received an i.v. injection of 1 ml of 1% Evan Blue containing 1 mg of DNP-BSA allergen. Blue spots started to appear within 10 minutes.

The ability of the best degranulation inhibiting peptide $K_2(AL)_8K_2$ to inhibit PCA was further evaluated in vivo. PCA is the outcome of passively administrated IgE that binds to mast cells in the skin. Upon the systemic administration of the allergen (DNP-BSA) together with Evan's Blue, it reaches the mast cells and crosslinks the FcεRI-bound IgE that in turn triggers degranulation of skin-mast cells. Amongst the materials that are released to the vicinity of the injection site there are vaso-dilating agents that allow the Evan Blue to accumulate at the IgE injection site, resulting in a blue colored mark. Therefore, to test the inhibitory activity of the $K_2(AL)_8K_2$ peptide, it was intra-dermally injected in the rat with the DNP-specific IgE, followed by an intravenous injection of DNP-BSA and Evans blue. As can be seen in FIG. 10, administration of the $K_2(AL)_8K_2$ peptide (and not irrelevant control peptide, data not shown) almost completely inhibited the PCA within 15-30 minutes in a dose-dependent manner.

Example 8

The Peptides of the Invention Inhibit Fatal Anaphylactic Shock

The inhibitory capacity of the $K_n(AL)_nK_n$ peptides was tested in the most rigorous manner for inhibition of otherwise fatal anaphylaxis. In this model, Balb/c mice were immunized by an i.p. injection of 100 μg OVA in 5 mg Alum and 1.5 μg pertussis, a protocol that favors IgE-type of response. Three weeks later the immunized mice received an i.v. injection of soluble OVA (3.5-5 μg), resulting in a rapid and aggressive anaphylactic shock. In this specific model, the immunized mice die within 10-20 minutes after the systemic (i.v.) OVA injection.

To test the ability of the peptides of the invention to inhibit anaphylactic shock formation, an i.v. injection of the $K_2(AL)_8K_2$ peptide at 10-15 mg/kg was administered, 30-45 minutes prior to the soluble OVA challenge. Strikingly, this single injection rescued 87% of the sensitized mice (Table 7). This dramatic protection (also observed by the $(AL)_6AK_2$ peptide) was found to be effective in the mice and could even be curative if given up to a few minutes following the soluble OVA challenge. In several mice that were protected by the $K_2(AL)_8K_2$ peptide, the protection lasted for at least 2 days. Peptide treated mice died of anaphylactic shock only after systemic injection of a very high dose of OVA. Still, the exact conditions for optimum protective activity need to be validated.

As negative controls, two different peptides were used. The first peptide $L(AL)_9K$ which did not show any activity in the in vitro models, failed also to give any protection in the in vivo model. The second peptide used was the $K_2(AL)_{10}AK_2$ a 25 mer with same charges and composition of the original 20 mer $K_2(AL)_8K_2$, differing only in length. This peptide gave some protection (50%) suggesting that the length is an important factor for the peptide activity (Table 7). Peptides mimicking transmembrane domains are usually 20 mer in length, suggesting that this specific peptide might not be fully inserted into the membrane.

TABLE 7

Effect of different peptides on the survival of mice after antigen (OVA) induced anaphylactic shock.

| Peptide | Survival of anaphylactic shock (%) |
|---|---|
| No peptide | 0 |
| $K_2(AL)_8K_2$ (SEQ ID NO: 1) | 87 (14/16) |
| $L(AL)_9K$ (SEQ ID NO: 13) | 0 |
| $K_2(AL)_{10}AK_2$ (SEQ ID NO: 17) | 50 |

Example 9

Toxicity and Specificity Assays

The group of $K_n(AL)_nK_n$ peptides in the concentrations used in this study was not toxic to cells nor to the experimental animals. Its incubation with RBL cells did not kill the cells and did not cause a growth arrest or degranulation. It also did not inhibit T cell responses in vitro such as IL-2 secretion following activation with allogeneic lymphocytes, anti-CD3+ anti-CD28 or Con-A (data not shown). Moreover, mice receiving high dosage of the $K_2(AL)_8K_2$ peptide (100 mg/kg, X10 over the effective dose), were not adversely affected by the peptides and did not show any pathological symptoms Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. An isolated peptide of 13-30 amino acids comprising the formula of $K_n(AX_1)_m X_2 K_n$, wherein $X_1$ is Leucine (L), $X_2$ is absent or Alanine, n, at each occurrence is independently 0-3 with the proviso that at least one terminal Lysine (K) is present, and m is 5-9.

2. The isolated peptide of claim 1, wherein a stretch of 1-3 Lysine residues is present at said peptide's N-terminus and C-terminus.

3. The isolated peptide of claim 1, comprising the formula of $K_n(AL)_m K_n$, wherein n, at each occurrence is independently 0-2 with the proviso that at least one terminal Lysine (K) is present, and m is 6-9.

4. The isolated peptide of claim 3 selected from the group consisting of: (SEQ ID NO: 1) KK(AL)$_8$KK; (SEQ ID NO: 2) (AL)$_9$KK; (SEQ ID NO: 3) K(AL)$_9$K; and (SEQ ID NO: 4) (AL)$_7$K.

5. The isolated peptide of claim 3, as set forth in SEQ ID NO: 1.

6. The isolated peptide of claim 1, comprising the formula of $K_n(AL)_m K_n$, wherein n, at each occurrence is independently 0-2 with the proviso that at least one terminal Lysine (K) is present, and m is 5-9.

7. The isolated peptide of claim 1 selected from the group consisting of: (SEQ ID NO: 5) KK(AL)$_5$AKK; (SEQ ID NO: 6) (AL)$_6$AKK; and (SEQ ID NO: 7) K(AL)$_6$AK.

8. The isolated peptide according to claim 1, wherein the peptide comprises at least one D amino acid.

9. A pharmaceutical composition comprising as an active ingredient an isolated peptide according to claim 1, and a pharmaceutically acceptable carrier.

10. A method of treating an inflammatory condition in a subject in need thereof comprising administering to the subject a therapeutically acceptable amount of the pharmaceutical composition of claim 9, wherein the inflammatory condition is selected from the group consisting of microbial infection, systemic inflammatory response syndrome (SIRS), sepsis, septicemia, septic shock, a mast cell-related disease, and an allergic reaction.

11. The method of claim 10, wherein the allergic reaction is an IgE-mediated allergic disorder.

12. The method of claim 11, wherein the IgE-mediated allergic disorder is selected from the group consisting of: allergy-induced asthma, hypersensitivity, eczema conjunctivitis, urticaria, rhinorrhea, rhinitis gastroenteritis, food allergies, pemphigus vulgaris, atopic dermatitis, eosinophilia and allergic bronchopulmonary aspergillosis.

13. A method of neutralizing the activity of lipopolysaccharides (LPS) endotoxin in a subject in need thereof comprising administering to the subject a pharmaceutically acceptable amount of the pharmaceutical composition of claim 9.

14. The method of claim 13, for preventing, neutralizing or reducing endotoxemia or endotoxin-induced septic shock.

* * * * *